US006507401B1

(12) United States Patent
Turner et al.

(10) Patent No.: US 6,507,401 B1
(45) Date of Patent: Jan. 14, 2003

(54) APPARATUS AND METHOD FOR ANALYZING FLUIDS

(75) Inventors: William Edward Turner, Palmyra, PA (US); Denis P. Biglin, Jr., Glastonbury, CT (US); John B. Cooper, Virginia Beach; Jeffrey F. Aust, Chesapeake, both of VA (US)

(73) Assignees: APS Technology, Inc., Cromwell, CT (US); Old Dominion University Research Foundation, Norfolk, VA (US)

( * ) Notice: Subject to any disclaimer, the term of this patent is extended or adjusted under 35 U.S.C. 154(b) by 0 days.

(21) Appl. No.: 09/453,003

(22) Filed: Dec. 2, 1999

(51) Int. Cl.$^7$ ............................................... G01N 21/64
(52) U.S. Cl. ...................................... 356/436; 356/417
(58) Field of Search ........................... 356/70, 317, 417

(56) References Cited

U.S. PATENT DOCUMENTS

| | | | |
|---|---|---|---|
| 2,334,475 A | 11/1943 | Claudet | 250/71 |
| 2,423,774 A | 7/1947 | Heigl | 250/83 |

(List continued on next page.)

FOREIGN PATENT DOCUMENTS

| | | |
|---|---|---|
| DE | 42 43 418 A1 | 6/1994 |
| EP | 0 215 648 A2 | 3/1985 |

(List continued on next page.)

OTHER PUBLICATIONS

Continuous on–line analyzer, *Flow Vision*, 1991, A1–A11.
Downare, T.D., "Visible and near–infrared fluorescence of crude oils," *Applied Spectroscopy*, 1995, 49, 754–764.
Flow vision on–line infrared analyzers, *Flow Vision*, 1991, B1–B7.
Flow vision analyzer, On line and research particle analysis, *Flow Vision*, 1991, 2 pages.
Kilham, L.B., "On–line particulate analysis of polymers and compounds: in–the–melt vs. finished product studies," *Polymers, Lamination and Coatings Conference Book 2*, 1986, 355–361 (abstract).
Mullins, O.C., "Linearity of near–infrared spectra of alkanes," *Applied Spectroscopy*, 1999, 6, No. 2000, 624–629.
Mullins, O.C. "Asphaltenes in crude oil: absorbers and/or scatterers in the near–infrared region?," *Am. Chem. Soc.*, 1990, 62, 508–514.
Plastics compounding for resin producers, formulators and compounders, *HBJ Plastics Publication*, 1987, 10(5), 4 pages.
Raman Solution 633, *Detection Limit Raman*, 1 page.
The dawn of a new age in on–line quality control, *Flow Vision*, 1991, 6 pages.
The Raman Solution 852, *Detection Limit Raman*, 2 pages.
The flow vision analyzer, On–line real time display with counting and size distribution analysis of particles in a moving stream or surface, *Flow Vision*, 1991, 4 pages.

*Primary Examiner*—Richard A. Rosenberger
(74) *Attorney, Agent, or Firm*—Woodcock Washburn LLP

(57) ABSTRACT

A method and apparatus for determining the concentration of a constituent in a fluid by directing a beam of light into the fluid and sensing the intensity of components of the light emerging from the fluid at various wavelengths. The light emerging from the fluid can be light that has been attenuated by absorption or induced by fluorescent radiation. The effect of scattering on the light is minimized by normalizing the component intensities, which are then applied to an algorithm incorporating weighting factors that weighs the influence that the intensity at each wavelength has on the determination of the concentration of the constituent for which the algorithm was developed. The algorithm is developed by a regression analysis based upon a plurality of known mixtures containing various concentrations of the constituent of interest.

53 Claims, 13 Drawing Sheets

U.S. PATENT DOCUMENTS

| | | | | |
|---|---|---|---|---|
| 2,425,531 | A | 8/1947 | Haseltine et al. | 88/14 |
| 3,371,574 | A | 3/1968 | Dwyer | 88/14 |
| 3,806,727 | A | 4/1974 | Leonard et al. | 250/301 |
| 3,842,270 | A | 10/1974 | Gregory et al. | 250/301 |
| 3,859,851 | A | 1/1975 | Urbanosky | 73/155 |
| 3,896,312 | A | 7/1975 | Brown et al. | 250/343 |
| 3,917,945 | A | 11/1975 | Sema et al. | 250/301 |
| 3,972,648 | A | 8/1976 | Sangster | 417/12 |
| 4,012,712 | A | 3/1977 | Nelligan | 340/18 CM |
| 4,023,201 | A | 5/1977 | Faulkner | 358/113 |
| 4,057,721 | A | 11/1977 | deVial et al. | 250/301 |
| 4,059,356 | A | 11/1977 | Kebabian | 356/204 |
| 4,227,083 | A | 10/1980 | Sherinski | 250/343 |
| 4,323,777 | A | 4/1982 | Baskins et al. | 250/339 |
| 4,370,886 | A | 2/1983 | Smith, Jr. et al. | 73/153 |
| 4,371,785 | A | 2/1983 | Pedersen | 250/343 |
| 4,375,164 | A | 3/1983 | Dodge et al. | 73/154 |
| 4,394,573 | A | 7/1983 | Correa et al. | 250/253 |
| 4,396,259 | A | 8/1983 | Miller | 351/158 |
| 4,399,359 | A | 8/1983 | Fertl et al. | 250/270 |
| 4,427,944 | A | 1/1984 | Chandler | 324/353 |
| 4,434,364 | A | 2/1984 | Correa et al. | 250/253 |
| 4,446,370 | A | 3/1984 | Gergely | 250/301 |
| 4,492,862 | A | 1/1985 | Grynberg et al. | 250/255 |
| 4,540,283 | A | 9/1985 | Bachalo | 356/336 |
| 4,547,774 | A * | 10/1985 | Gould | 234/854.7 |
| 4,587,640 | A | 5/1986 | DiFoggio | 367/30 |
| 4,598,290 | A | 7/1986 | Collins et al. | 340/850 |
| 4,602,160 | A | 7/1986 | Mactaggart | 250/341 |
| 4,608,859 | A | 9/1986 | Rockley | 73/153 |
| 4,609,821 | A | 9/1986 | Summers | 250/255 |
| 4,620,284 | A | 10/1986 | Schnell et al. | 364/498 |
| 4,659,218 | A | 4/1987 | de Lasa et al. | 356/133 |
| 4,663,961 | A | 5/1987 | Nelson et al. | 73/24 |
| 4,766,543 | A | 8/1988 | Schmidt | 364/422 |
| 4,770,243 | A | 9/1988 | Fouillout et al. | 166/53 |
| 4,800,279 | A | 1/1989 | Hieftje et al. | 250/339 |
| 4,814,614 | A | 3/1989 | Tsui | 250/301 |
| 4,825,073 | A | 4/1989 | Smith, Jr. et al. | 250/260 |
| 4,874,243 | A | 10/1989 | Perren | 356/342 |
| 4,891,640 | A | 1/1990 | Ip | 340/853 |
| 4,893,253 | A * | 1/1990 | Lodder | 702/28 |
| 4,939,648 | A | 7/1990 | O'Neill et al. | 364/422 |
| 4,977,319 | A | 12/1990 | Supernaw | 250/255 |
| 4,990,773 | A | 2/1991 | Supernaw et al. | 250/255 |
| 4,994,671 | A * | 2/1991 | Safinya et al. | 250/225 |
| 4,994,747 | A | 2/1991 | Stolarczyk | 324/334 |
| 5,035,581 | A | 7/1991 | McGuire et al. | 417/36 |
| 5,049,738 | A | 9/1991 | Gergely et al. | 250/301 |
| 5,065,019 | A | 11/1991 | Darilek et al. | 250/301 |
| 5,084,617 | A | 1/1992 | Gergely | 250/253 |
| 5,095,758 | A | 3/1992 | Cox et al. | 73/861.04 |
| 5,104,545 | A | 4/1992 | Means et al. | 210/650 |
| 5,105,085 | A | 4/1992 | McGuire et al. | 250/343 |
| 5,112,127 | A | 5/1992 | Carrabba et al. | 356/301 |
| 5,128,882 | A | 7/1992 | Cooper et al. | 364/550 |
| 5,135,656 | A | 8/1992 | Means et al. | 210/650 |
| 5,145,785 | A | 9/1992 | Maggard et al. | 436/8 |
| 5,166,747 | A | 11/1992 | Schroeder et al. | 356/326 |
| 5,167,149 | A | 12/1992 | Mullins et al. | 73/155 |
| 5,198,871 | A | 3/1993 | Hill, Jr. et al. | 356/318 |
| 5,201,220 | A | 4/1993 | Mullins et al. | 73/155 |
| 5,237,539 | A | 8/1993 | Selman | 367/69 |
| 5,237,857 | A | 8/1993 | Dobson et al. | 73/61.44 |
| 5,253,271 | A | 10/1993 | Montgomery | 375/59 |
| 5,266,800 | A * | 11/1993 | Mullins | 250/256 |
| 5,272,350 | A | 12/1993 | Solari et al. | 250/551 |
| 5,275,038 | A | 1/1994 | Sizer et al. | 73/151 |
| 5,285,204 | A | 2/1994 | Sas-Jaworsky | 340/854.9 |
| 5,322,126 | A | 6/1994 | Scott, III | 166/308 |
| 5,327,211 | A | 7/1994 | Carron et al. | 356/301 |
| 5,331,156 | A | 7/1994 | Hines et al. | 250/256 |
| 5,349,189 | A | 9/1994 | Maggard | 250/339.07 |
| 5,351,532 | A | 10/1994 | Hager | 73/153 |
| 5,360,975 | A | 11/1994 | Stoller | 250/262 |
| 5,381,002 | A | 1/1995 | Morrow et al. | 250/301 |
| 5,406,078 | A | 4/1995 | Jacobson | 250/261 |
| 5,410,152 | A | 4/1995 | Gadeken | 250/260 |
| 5,412,581 | A | 5/1995 | Tackett | 364/498 |
| 5,413,179 | A | 5/1995 | Scott, III | 166/308 |
| 5,418,614 | A | 5/1995 | Brost et al. | 356/434 |
| 5,419,188 | A | 5/1995 | Rademaker et al. | 73/151 |
| 5,424,959 | A | 6/1995 | Reyers et al. | 364/498 |
| 5,441,110 | A | 8/1995 | Scott, III | 166/308 |
| 5,461,236 | A | 10/1995 | Gram et al. | 250/461.1 |
| 5,467,823 | A | 11/1995 | Babour et al. | 166/250.01 |
| 5,485,743 | A | 1/1996 | Taherian et al. | 73/61.44 |
| 5,485,745 | A | 1/1996 | Rademaker et al. | 73/151 |
| 5,495,547 | A | 2/1996 | Rafie et al. | 385/101 |
| 5,517,024 | A | 5/1996 | Mullins et al. | 250/254 |
| 5,519,214 | A | 5/1996 | Houwen et al. | 250/256 |
| 5,543,616 | A | 8/1996 | Eadington et al. | 250/55 |
| 5,591,922 | A | 1/1997 | Segeral et al. | 73/861.04 |
| 5,608,170 | A | 3/1997 | Atkinson et al. | 73/861.04 |
| 5,656,810 | A | 8/1997 | Alfano et al. | 250/301 |
| 5,686,724 | A | 11/1997 | Spilker et al. | 250/255 |
| 5,693,152 | A | 12/1997 | Carron | 148/271 |
| 5,712,481 | A | 1/1998 | Welch et al. | 250/339.12 |
| 5,717,209 | A | 2/1998 | Bigman et al. | 250/339.12 |
| 5,729,013 | A | 3/1998 | Bergren, III | 250/255 |
| 5,736,637 | A | 4/1998 | Evans et al. | 73/152.31 |
| 5,742,064 | A | 4/1998 | Infante | 250/458.1 |
| 5,763,883 | A | 6/1998 | Descales et al. | 250/339.09 |
| 5,780,850 | A | 7/1998 | DeLaune et al. | 250/255 |
| 5,831,743 | A | 11/1998 | Ramos et al. | 356/445 |
| 5,856,869 | A | 1/1999 | Cooper et al. | 356/301 |
| 5,859,430 | A | 1/1999 | Mullins et al. | 250/255 |
| 5,939,717 | A | 8/1999 | Mullins | 250/255 |
| 6,016,191 | A * | 1/2000 | Ramos et al. | 356/70 |
| 6,023,340 | A | 2/2000 | Wu et al. | 356/432 |
| 6,085,153 | A * | 7/2000 | Hirsh et al. | 702/23 |

FOREIGN PATENT DOCUMENTS

| | | |
|---|---|---|
| GB | 2 337 107 | 10/1999 |
| WO | WO 97/11402 | 3/1997 |
| WO | WO 97/35171 | 9/1997 |
| WO | WO 97/48972 | 12/1997 |
| WO | WO 98/25128 | 6/1998 |
| WO | WO 98/36265 | 8/1998 |

* cited by examiner

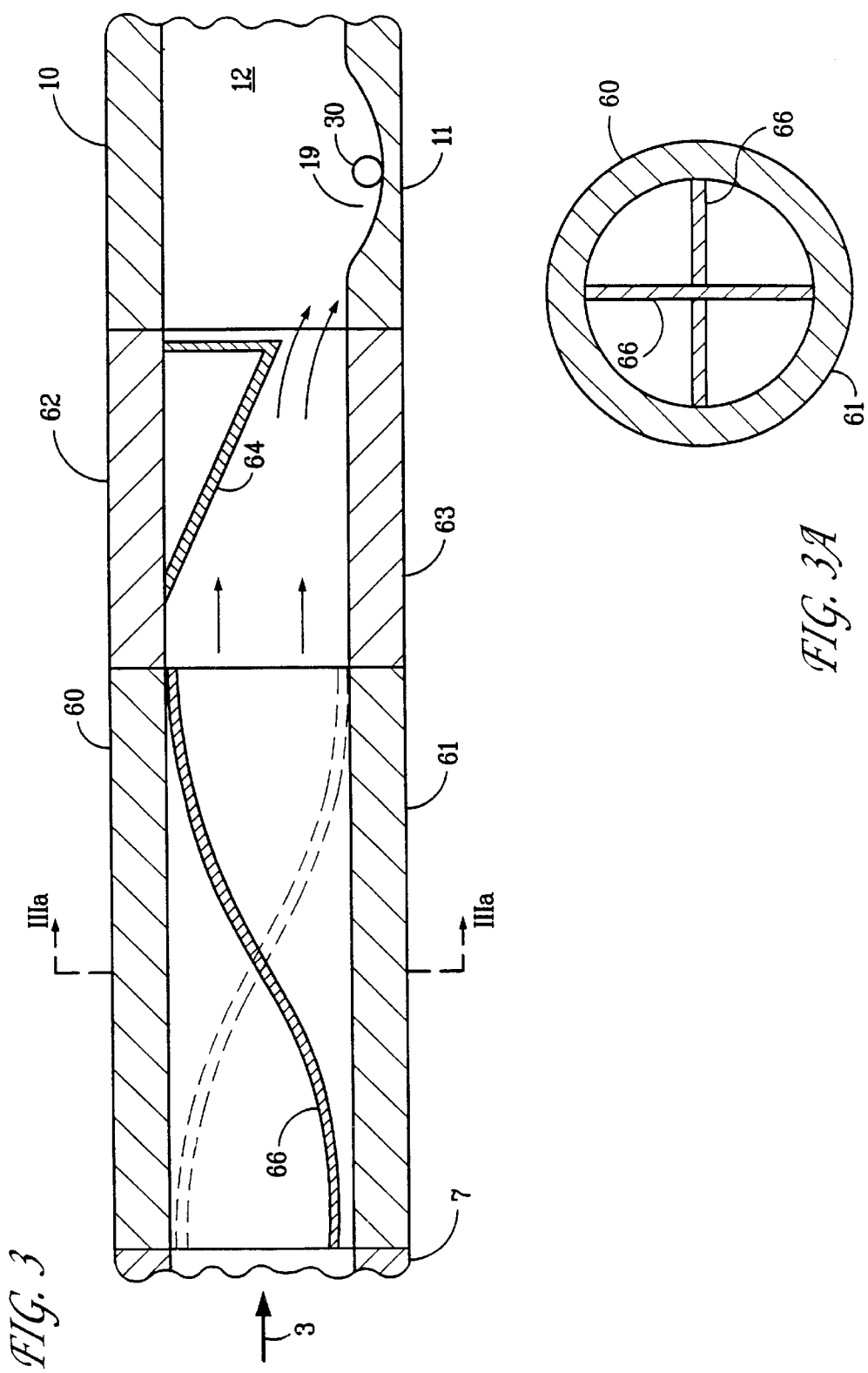

APPARATUS AND METHOD FOR ANALYZING FLUIDS

FIELD OF THE INVENTION

The current invention is directed to the analysis of fluids. More specifically, the current invention is directed to the compositional analysis of fluids, such as fluids produced by oil wells, that contain constituents that fluoresce and/or absorb radiation, such as near-infrared radiation.

BACKGROUND OF THE INVENTION

Monitoring of the fluids produced by an oil well, such as compositional analysis, provides valuable information that allows production to be optimized. In the past, such monitoring was performed by analyzing fluid samples brought to the surface, typically using techniques such as ultraviolet-visible (UV-Vis) absorbance spectroscopy, infrared (IR) absorbance spectroscopy, UV fluorescence spectroscopy, nuclear magnetic resonance spectroscopy, mass spectrometry, and gas chromatography.

Unfortunately, these traditional surface fluid analysis techniques are of limited value in many wells created using modem drilling and production methods. This is so because modem methods often result in the creation of complex and/or difficult to monitor wells, such as multizone, horizontal, or multilateral wells. In such wells, fluid produced from different zones of the well may be combined downhole so that the fluid discharged at the surface is a mixture. Analysis of this mixture provides little information concerning the component of the fluid production associated with any of the individual zones of the well, which is necessary to maximize the overall production of oil while minimizing the production of water. For example, if one zone were producing fluid with a high water content, a control device could be operated to limit or cease production from that zone. Subsurface monitoring at the source is also advantageous where accurate knowledge of various field's production rates are required. For example, in subsea applications, fluid from different reservoirs may be combined at a subsea manifold. Production monitoring at this point is desirable to allow the operator to make control decisions regarding individual wells.

Another disadvantage of surface techniques is that they analyze the fluid after it has flowed through a long production tubing, which can alter the phase properties of the fluid (e.g., induce slugging). By contrast, downhole analysis provides real time data on conditions occurring at the point of production in the well.

Consequently, it would be desirable to provide a system and method for analyzing fluid produced in each individual zone of the well prior to intermixing—that is, in a downhole environment.

The ability to remotely sense the presence of certain fluids, such as oil, in a flowing stream, is also desirable in situations other than in oil wells. For example, it is sometimes desirable to determine when a fluid, such as discharge water, that should not contain oil has become contaminated with oil. Consequently, it would be desirable to provide a system and method for analyzing the presence of certain fluids in a flowing stream.

When light strikes a fluid, several phenomena may occur. A portion of the light may be reflected from the surface, while another portion will enter the fluid. The portion of the light entering the fluid may be transmitted through the fluid or subjected to scattering or absorption. Very often, all of these mechanisms occur simultaneously.

Light may scatter as a result of several different mechanisms. If more than one phase is present in the fluid, light will be scattered by reflection and refraction at the interfaces between the phases. Scattering will also occur as a result of the Rayleigh mechanism. Light scattered by the Rayleigh mechanism has the same wavelength as that of the incident light. In some substances, such as oil, scattering also occurs by the Raman phenomenon. Raman scattering produces extremely low intensity light (relative to the intensity of the incident light) having wavelengths both above and below that of the incident light, so that even monochromatic light yields scattered light in a range of wavelengths. Thus, when analyzed by a spectrograph, Raman scattering produces lines on both sides of the Rayleigh line that are a characteristic of the substance and upon which the light is incident can be used its composition.

Previously, it has been proposed to use Raman scattering to determine the composition of certain types of hydrocarbons in refineries, such as disclosed in U.S. Pat. No. 4,620,284 (Schnell et al.). However, Raman analysis cannot be used to determine the composition of a mixture of crude oil and water, such as that flowing through a well, for two reasons. First, crude oil is highly fluorescent so the fluorescent radiation, which has a longer wavelength than the incident light, would overwhelm the Raman signal even when using a near infrared excitation source. Second, the light emitted as a result of Raman scattering is too low in intensity to be transmitted to the surface for analysis, while the down hole environment is too harsh to permit the use of the sensitive equipment, such as a spectrograph and charged couple device, necessary to conduct a Raman analysis down hole.

In addition to scattering, a portion of the light entering the fluid may be absorbed. The amount of light absorbed at a given wavelength is a characteristic of the substance. Therefore, the constituents of a substance can be determined by comparing the spectrum of the light directed into the fluid with that of the light that has been transmitted through it so as to determine the spectrum of the light absorbed by the fluid. This spectrum may be expressed, for example, as $-\log_{10}$ of the ratio of the light directed to the fluid and the light transmitted through the fluid. Although compositional analyses using absorption have been proposed in the past, they suffer from the fact that the intensity of the light transmitted through the fluid depends on scattering, as well as absorption. Whereas absorption is primarily a function of the constituents of the fluid, scattering also depends on the physical form of those constituents. For example, in an emulsion, such as a mixture of water and oil, the more finely dispersed the oil droplets the greater the scattering. The increase in scatting associated with the reduction in droplet size will reduce the intensity of the transmitted light, despite the fact that the composition of the fluid, in a quantitative sense, has remained unchanged. Scattering can, therefore, lead to significant errors in systems measuring the absorption spectra of the fluid.

U.S. Pat. No. 4,994,671 (Safinya et al.) discloses a method for analyzing the composition of fluid in a well by suspending within the well a tool that contains a spectrograph and an incandescent tungsten-halogen lamp. The lamp is characterized as being relatively bright in the 1000 to 2500 nm range and down to about 500 nm and having acceptable emissions from 350 to 500 nm. The lamp directs light onto a sample of fluid that is admitted into the tool. Different sections of a fiber optic bundle receive the light transmitted across the fluid sample, as well as the light back-scattered from the sample. The spectra of both the transmitted light and the back scattered light are measured by a spectrograph and the data are digitized and transmitted electronically to a computer at the surface. Two absorption spectra for the fluid are determined by dividing the transmitted light spectrum and the back scattered light spectrum by the spectrum of the source light. If the fluid is sufficiently transparent to transmit an adequate amount of light through it, Safinya recommends the use of the transmitted light; otherwise the back-scattered light may be used. The computer determines the constituents of the fluid sample by comparing the transmitted or back-scattered absorption spectra to a data base containing reference spectra for water, gas and various types of oils, and using a least squares or principal component analysis method. Since the spectra may vary with the temperature and pressure, Safinya discloses that in order to obtain an accurate analysis, the data base should contain reference spectra for the various constituents at a variety of pressures and temperatures. Unfortunately, Safinya's method suffers from a variety of drawbacks that have made it unsuitable for use in practical applications.

First, as indicated in U.S. Pat. No. 5,266,800 (Mullins), the computations necessary to perform the analysis taught by Safinya are computationally intensive and required an extensive data base of spectra for water, gas and oils.

Second, and perhaps more importantly, Safinya does not account for the effect of variations arising from scattering. The flow of a multicomponent fluid (e.g., oil, water and gas) through a production well has very complex multiphase properties. Variations will occur not only in terms of the relative proportion of the constituents but also in multiphase characteristics, such as droplet or bubble size and the composition of the continuous and dispersed phases (e.g., oil and gas bubbles dispersed in water, oil droplets dispersed in gases, etc.). Additionally, there may be particulate matter suspended in the fluid, which can add to the scattering. As discussed above, variations in these physical characteristics of the fluid will cause variations in the intensity of the transmitted or back scattered light that, according to Safinya's method, will cause an apparent, but erroneous, change in the composition of the fluid. For example, suppose that the spectrum is obtained of a fluid flowing through a well that is initially a 50/50 mixture of oil and water, with the water occurring in relatively large droplets. Further suppose, although this is not by any means to be expected, that comparison to the spectra in the data base using Safinya's method results in the correct determination of the composition. If the fluid remains a 50/50 mixture but the water and oil become more finely dispersed, the intensity of the transmitted light will decrease at all wave lengths, including the intensity of the light in the wave lengths associated with water, which will be interpreted as a greater absorption in the water-associated wave lengths. This, in turn, will lead to the erroneous conclusion that the concentration of water in the fluid has increased.

U.S. Pat. No. 5,166,747 (Schroeder) recognizes that scattering in Safinya's method can cause the intensity of the transmitted light to undergo swings so wide that they cannot be handled by the spectrograph. Schroeder's approach to this challenge was, through an opto/mechanical means, to redistribute the composition of the transmitted light reaching the spectral analyzer. Through optical diffusers or misalignment of the input and output fibers, the spectral analyzer received less directly transmitted light and more forward scattered light. The forward scattered light still indicated the absorbance of the sample, but it is of reduced intensity. The weaker signal was an acceptable tradeoff for signal stability. However, this approach is not feasible where the light source and spectral analyzer are at the surface. In such circumstances, the signal intensity is of paramount concern due to the losses that can occur if the sampling portion of the sensor is many kilometers from the surface. Also, the potential for errors due to scatter will still occur and, perhaps, be even greater than those associated with Safinya's method because the strength of the original signal is reduced.

SUMMARY OF THE INVENTION

It is an object of the current invention to provide a method for determining the concentration of a constituent, such as oil or gas, in a fluid flowing in a remote location, such as downhole in an oil well. This and other objects is accomplished in a method of determining the concentration of at least one predetermined constituent in a fluid flowing through a downhole portion a well, comprising the steps of (i) generating a beam of light, (ii) directing the beam of light into the fluid flowing through the downhole portion of the well so as to cause light to emerge from the fluid, the emerging light having been scattered by the fluid and comprised of components each of which has a different wavelength, (iii) transmitting at least a portion of the emerging light to a location proximate to the surface of the earth, (iv) measuring the intensity of each of at least a portion of the components of the transmitted light, each of the light components in the portion of light components having a wavelength falling within a predetermined range of wavelengths, the light component intensity measurements being conducted at the location proximate the surface, (v) normalizing at least those of the measured light component intensities having selected wavelengths so as to reduce the effect of the scattering of the light components on the measured intensities, (vii) exponentially raising and then multiplying each of the normalized light component intensities at the selected wavelengths by a predetermined weighting factor based upon its respective wavelength, and (viii) summing the weighted and normalized light component intensities at the selected wavelengths so as to calculate the concentration of the constituent.

In one embodiment, the method further comprises the step of determining the weighting factors by (i) directing a calibration beam of light into a plurality of fluid calibration mixtures so as to cause light to emerge from each of the calibration mixtures that is comprised of components each of which has a different wavelength, with each of the calibration mixtures containing predetermined varying concentrations of the constituent, (ii) measuring the intensity of each of the components of the light emerging from the calibration mixtures having a wavelength falling within the predetermined range of wavelengths, (iii) normalizing at least a selected portion of the measured intensities of the light components emerging from the calibration mixtures, and (iv) performing a regression analysis on the normalized intensities of the calibration mixtures so as to determine the weighting factors.

The invention also encompasses an apparatus for determining the concentration of a predetermined constituent in a fluid flowing through a downhole portion a well, comprising (i) means for generating a beam of light, (ii) means for directing the beam of light into the fluid flowing through the downhole portion of the well so as to cause light to emerge from the fluid which light is comprised of components each of which having a different wavelength and that has been scattered by the fluid prior to emerging therefrom, (iii)

means for transmitting at least a portion of the emerging light to a location remote from the downhole portion of the well, (iv) means for measuring the intensity of each of the components of the transmitted light having a wavelength falling within a predetermined range of wavelengths at the remote location, (v) means for exponentially raising and normalizing at least a selected portion of the measured component intensities so as to minimize the effect of the scattering to the light emerging from the fluid has been subjected on the component intensities, (vi) means for determining the concentration of the constituent based upon the normalized component intensities.

In one embodiment, the apparatus further comprises a computer, and the means for means for normalizing the selected portion of the measured component intensities and the means for determining the concentration of the constituents comprises software programmed into the computer.

BRIEF DESCRIPTION OF THE DRAWINGS

FIG. 3 is a longitudinal cross-section taken along line III—III shown in FIG. 2.

FIG. 3a is a transverse cross-section through the mixer shown in FIG. 3, taken along line IIIa—IIIa.

DESCRIPTION OF THE PREFERRED EMBODIMENT

Figure 1:
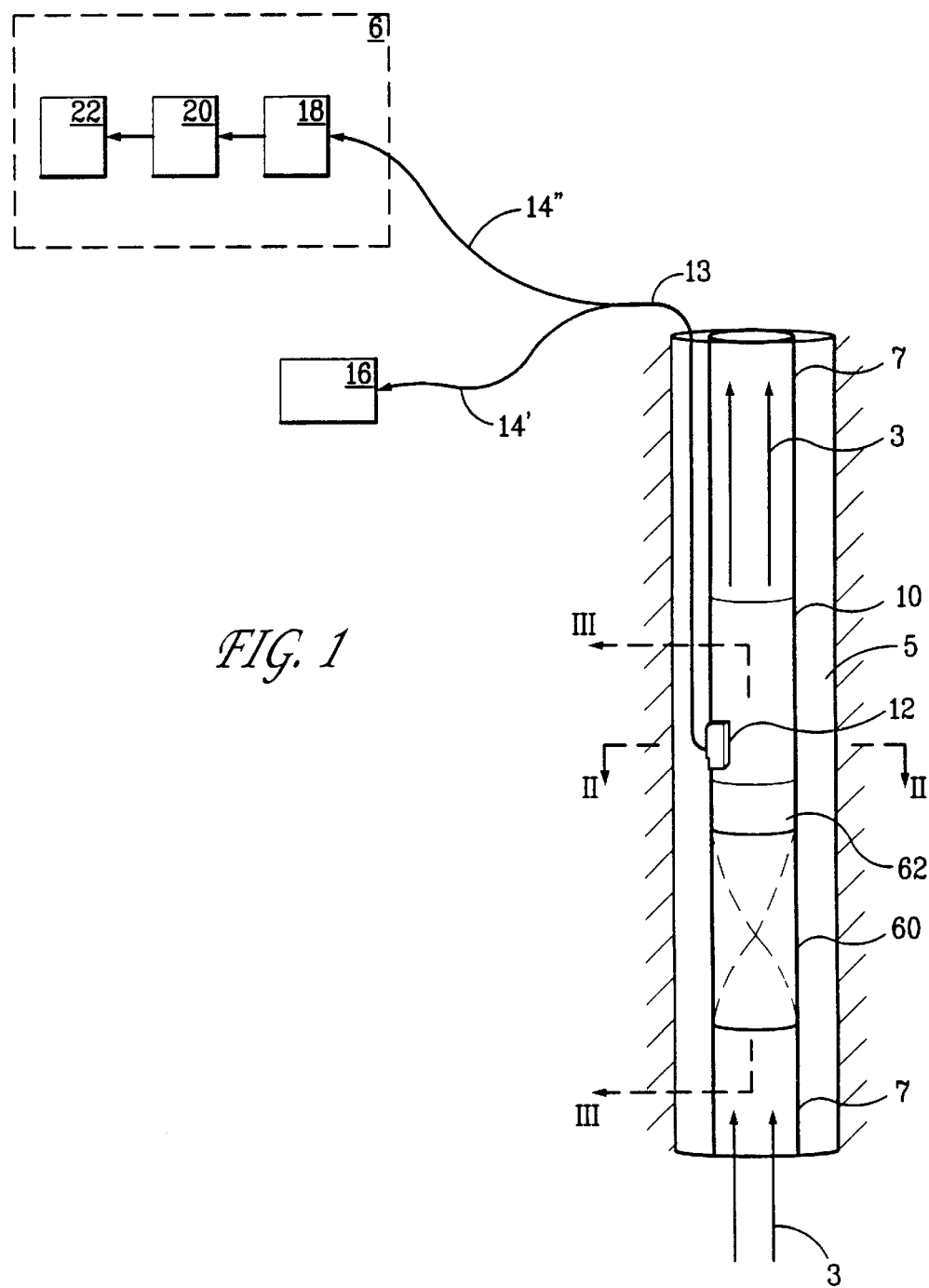
FIG. 1 is schematic diagram of the fluid analysis system according to the current invention installed in a section of pipe.

According to the current invention, the concentration of certain constituents in a fluid can be determined by directing light to the fluid, sensing the light emerging from the fluid, measuring the relative intensity of the components of the sensed light at selected wavelengths, and then treating these relative component intensities according to an algorithm, developed for the particular fluid being analyzed, that weights the component intensities using predetermined weighting factors based on the wavelength associated with each component. As such, the method of the current invention realizes four important advantages over prior methods of analysis. First, once the algorithm has been properly generated, only the components of the light intensity at wavelengths within a predetermined range need be analyzed—that is, it is not necessary to analyze the entire spectrum of the light emerging from the fluid being analyzed. Second, it is not necessary to maintain a large data base of spectra of fluids of known compositions. Third, it is not necessary to compare the measured data to a data base of the spectra of fluids of known composition. Fourth, the effects of scattering are eliminated by normalizing the individual intensities of the emerging light at each of the selected wavelengths.

According to the current invention, the algorithm to be used in calculating the concentration of a particular constituent can be developed by measuring the intensity of the components of the light emerging from various known mixtures of the fluids to be analyzed over a range of wavelengths. These mixtures are formed by varying the concentration of the particular constituents in the fluid in a known way. After normalizing the component intensities, a regression analysis, such as a partial least squares regression, is used to determine the weighting factors that indicate the weight to be attached to the normalized component intensity at each wavelength. Based on these weighting factors, an algorithm is developed for calculating the concentration of the constituent.

As discussed in detail below, in the practice of the current invention, either the phenomenon associated with the attenuation of radiation (e.g., as a result of absorption) or the excitation of fluorescent radiation may be used to determine the concentration of a particular constituent of the fluid. In particular, a beam of light is directed to the fluid. As a result of its passing through the fluid, the emerging light may be attenuated as a result of absorption and/or scattering. In addition, the light may induce fluorescence. Thus, compared to the light directed to the fluid, the light emerging from the fluid will be attenuated and/or comprises fluorescent radiation. The analysis of the emerging light permits the determination of concentration.

Whether the attenuation or fluorescence phenomenon is used to determine concentration depends on the constituent whose concentration is to be determined. The concentration of oil, for example, can be determined using either method. The concentrations of water and natural gas, which do not fluoresce, can only be directly determined using the attenuation method. When using the attenuation method, the light directed to the fluid should encompass a broad range of wavelengths. However, when the fluorescence method is used, the wavelength of the light directed to the fluid should lie within a narrow range, and preferably the light should be monochromatic. In some circumstances, such as when remotely determining the concentration of mixtures of oil, water and/or gas using the attenuation method, the light directed to the fluid is preferably in the near infrared ("near-IR") range—that is, having a wavelength from approximately 800 nm to 3000 nm.

In both the attenuation and fluorescence method, analysis of the emerging light is based on measurement of the intensity of its components at various predetermined wavelengths. Importantly, the measured intensities are normalized to minimize the errors resulting from scattering. When the attenuation method is used, each of the measured component intensities is preferably normalized by dividing it by an intensity characteristic associated with all, or at least most, of the components of the emerging light within a predetermined range of wavelength. When the fluorescence method is used, normalization is preferably accomplished by dividing the measured component intensities by an intensity characteristic of the laser light used to induce the fluorescence.

I. Analysis Based on Light Attenuation

As discussed above, as the light travels through the fluid, a variety of phenomena arise. Some of the components of the light at discrete wavelengths (or wavelength ranges) are absorbed depending to the chemical constitution of the fluid. In addition, some of the light is scattered in all directions due to the physical constitution of the fluid (emulsions, bubbles, binary mixtures, etc.), and some of the light is transmitted. Thus, the light entering the fluid is either absorbed, scattered, or transmitted through it.

The amount of light absorbed at a given wavelength is a characteristic of the substance through which the light is travels. While the light that is absorbed cannot be directly measured, the light emerging from the fluid can be measured. As a result of absorption, the intensity of the emerging light will be reduced or "attenuated." The amount of attenuation of the light for any given composition will varying as a function of its wavelength. Thus, for a given source light spectrum, evaluating the intensity of the components of the emerging light at selected wavelengths provides information about the composition of the fluid.

Scattering also causes attenuation of the light intensity. However, whereas attenuation as a result of absorption causes relative changes in the light intensity as a function of wavelength, i.e., there is a change in the shape of the broadband spectrum, attenuation due to the scattering of light is much less dependent on its absolute wavelength; it has a slow, monotonic dependence on wavelength. The scattering of the light, therefore, results in a drop in the light intensity at all wavelengths so that at any given wavelength, the intensity does not change appreciably relative to the intensity at other wavelengths. For fluids which both scatter and absorb light, the net result is that even though the absolute magnitude of the collected light as a function of wavelength it is not uniquely related to chemical composition, the relative light intensity as a function of wavelength is related to the chemical composition.

Therefore, according to the current invention, the effects of scattering can be effectively eliminated by normalizing the intensity of the collected light components at each wavelength utilized in the algorithm to the intensity over a broad band of wavelengths. Thus, an analysis of the relative attenuated components of the light emerging from the fluid can be used to accurately determine the concentration of its constituents, despite the simultaneous presence of scattering.

When the attenuation method of analysis is used, the light directed to the fluid preferably encompasses a broad band of wavelengths that, most preferably, is sufficiently broad to encompass all, or at least most, of the major absorption peaks associated with the constituents whose concentration is to be determined. For example, oil and natural gas have absorption peaks at 1200 nm and 1400 nm. Water has absorption peaks at 1150 nm and 1450 nm. Thus, the light should have wavelengths that at least encompass the 300 nm range as associated with these peaks (i.e., from 1150 nm to 1450 nm). Thus, in the case of mixtures of oil, water, and gas, the light directed to the fluid preferably has wavelengths in the near-IR range—that is, having a wavelength from approximately 800 nm to 3000 nm. More preferably, the light is in the range of about 900 nm to 2000 nm, more preferably still in the range of about 1100 nm to 1800 nm, and most preferably in the range of about 1100 nm to 1550 nm.

II. Analysis Based on Fluorescence

Depending upon on the material, the absorption of light may not only result in attenuation of the light intensity at certain wavelengths but may also result in generation of radiation at other wavelengths, specifically, due to fluorescence. Fluorescence is a type of luminescence—that is, light emitted by a process other than combustion or incandescence. When a flourescent substance is illuminated with light of the appropriate wavelength it absorbs energy which, in turn, excites the absorbing species to a higher energy electronic state. When the absorbing species returns to its electronic ground state, a photon of light is emitted. If the excited state from which the absorbing species decays has the same multiplicity as the ground state, the time between absorption and emission is relatively short and the process is called fluorescence. If the excited state from which the absorbing species decays has a different multiplicity from that of the ground state, the time interval is relatively long, and the process is referred to as phosphorescence. The light generated by fluorescence is always of longer wavelength than the incident light. Thus, in fluorescence, the absorption of light of one wavelength results in the emission of light of longer wavelengths.

Certain molecular arrangements within fluorescent substances, called chromophores, are the centers of fluorescent activity. Not all chromophores respond to light in the same way. In general, compounds with fused aromatic rings or compounds with a greater number of conjugated multiple bonds, such as crude oil, can fluoresce when subjected to light at longer wavelengths, specifically, in the visible to near-IR range. Less complex, low molecular weight compounds, such as the simple hydrocarbons found in natural gas, either do not fluoresce or fluoresce only at shorter wavelengths (in the ultra violet range) but not in the near-IR range. Water does not fluoresce. Other substances that do not fluoresce when excited by light in the near-IR range are sand and silt.

In general, using excitation light having shorter wavelengths will result in fluorescent radiation of greater intensity, making analysis easier. However, according to the current invention, the excitation light from the light source is generated at one location, preferably the surface, and transmitted through fiber optic cables over long distances to fluid at a remote location, such as downhole in an oil well. Light having short wavelengths, such as ultraviolet radiation, is difficult to transmit over such long distances and can result in excessive Raman scattering. By contrast, light in the near-IR range can be readily transmitted over long distances. In addition, shorter wavelength light may induce fluorescence in too many substances, making analysis of a particular constituent more difficult. In any event, near-IR excitation light causes oil, but not natural gas or water, to emit relatively intense fluorescent radiation. Consequently, according to the current invention, the concentration of oil is preferably determined using excitation light having a wavelength within or somewhat below the near-IR range.

When the fluorescence method is used, laser light having a relatively narrow wavelength band, and preferably 2 nm FWHM (i.e., full width at half maximum) or less, is directed to the fluid. Preferably, the source should emit light having wavelengths from somewhat below the near-IR range to about the mid near-IR range—that is, from about 500 nm to 1700 nm range. More preferably, the excitation light should be in the range of about the 600 nm to 1000 nm, more preferably still in the range of about the 780 nm to 900 nm, such as laser light having a wavelength of about 780 nm, 808 nm, or 852 nm.

As the laser light passes through the fluid, some of the light is absorbed by and re-emitted as fluorescent light at longer wavelengths than the absorbed light. Some of this fluorescent light is collected, along with some of the laser light that was transmitted through the fluid. For fluids that are highly scattering, the collected laser light intensity will be lower than for fluids that are not highly scattering since in the latter case a greater percentage of the laser light will be collected. Consequently, the laser light scattered by the fluid can be used as a means for monitoring its scattering characteristics.

The collected fluorescence light will be dependent on both the concentration of fluorescent species present in the fluid and the scattering properties of the fluid. As the concentration of fluorescent species increases, the collected fluorescent light will increase. As the scattering characteristics of the fluid increase, the collected fluorescent light will decrease. Thus, the influence of the scattering properties of the fluid can be corrected for by normalizing the collected fluorescent intensity to the collected laser intensity. (In some circumstances, it may also be desirable to normalize the collected laser intensity itself by the laser intensity at the surface, in order to correct for optical power fluctuations in the laser.) In any event, in the fluorescence method of analysis, evaluation of the normalized intensity of the fluorescent light emitted by the fluid can be used to accurately determine the concentration of its constituents, despite the presence of scattering.

III. Apparatus

A. Hardware

One embodiment of an apparatus according to the current invention is shown in FIG. 1 applied to an instrumented section of pipe 10, which in some applications may be incorporated into production piping 7 disposed in a well bore 5, through which the fluid 3 to be analyzed flows. Depending on the detailed components selected, each of which is discussed further below, the apparatus shown in FIG. 1 can be optimized for use with either the attenuation or fluorescence methods of analysis.

1. Sensor

As shown in FIG. 1, the instrumented pipe section 10 comprises a sensor 12 that has been incorporated into the pipe. Although only one sensor 12 is shown in FIG. 1, it may be desirable to incorporate a number of sensors into the instrumented section 10, for example, by spacing two or more sensors circumferentially around the pipe at the same axial location and/or spacing two or more sensors axially along the pipe. The use of multiple sensors 12 will reduce errors associated with the fact that the fluid flowing through the instrumented section 10 may not be uniform across its cross-section or along the length of the section.

Figure 2:
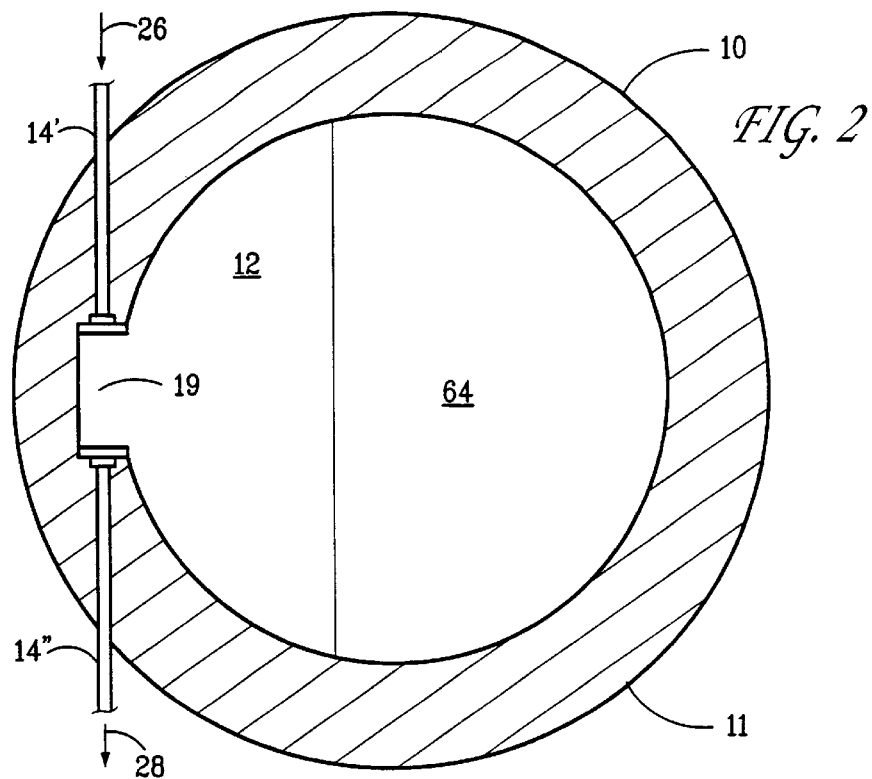
FIG. 2 is a transverse cross-section through the sensor shown in FIG. 1, taken along line II—II.
Figure 2A:
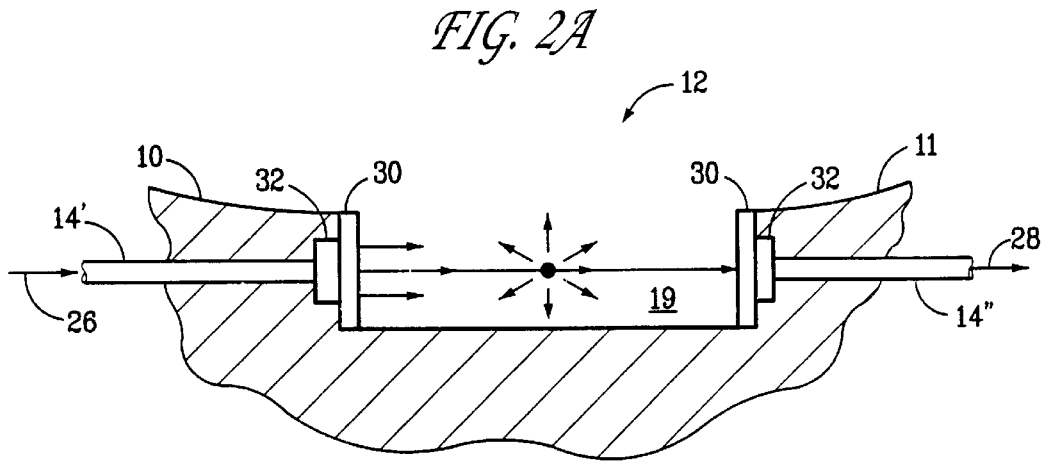
FIG. 2a is a detailed view of the sensor shown in FIG. 2.

A diagram of one sensor 12 suitable for use in the current invention is shown in FIGS. 2 and 2a and comprises a notch 19 formed in the inner wall of the pipe section 10. Optically transparent windows 30 are formed on opposing walls of the notch 19. A focusing lens 32, to which fiber optics 14 are coupled, is located behind each window 30. The light 26 from the source 16 exits the first fiber optic 14', passes through the first lens 32, and then the first window 30. The light subsequently passes into and interacts with the fluid stream 3. As shown in FIG. 2a, the light emerging from the fluid stream passes through the second window 30 and is focused by the second lens 32 so that it is collected by the second fiber optic 14".

As shown in FIG. 1, in some applications, it may be desirable to incorporate a mixing device 60 upstream of the instrumented section 10 so as to ensure adequate mixing of the fluid 3 to be measured. As shown in FIGS. 3 and 3a, the mixer 60 may comprise a section of piping 61 incorporated into the production piping 7 and into which helically extending mixing vanes 66 have been installed to swirl the fluid, thereby ensuring adequate mixing of the constituents before they reach the instrumented section 10.

As also shown in FIG. 1, it may also be desirable in some applications to incorporate a diverter section 62 upstream of the instrumented section 10 to ensure the proper flow of fluid 3 into the notch 19. As shown in FIG. 3, the diverter 62 may comprise a section of piping 63 incorporated into the production piping 7 and into which a baffle 64 has been installed. The baffle 64 is preferably angled toward the notch 19 of the sensor 12, most preferably at an angle with respect to the axis of the piping that is equal to or greater than the angle of the sloping side wall 19 of the notch, so as to deflect at least a portion, preferably a major portion, of the fluid 3 so that it is directed into the notch 19. This not only ensures that the fluid flowing through the notch 19 is representative of the fluid 3 flowing through the production piping 7 but also ensures that the fluid in the notch is not stagnant so as to flush the notch and prevent the buildup of deposits or debris that could interfere with the operation of the sensor 10.

The sections of piping forming the mixer 60, diverter 62 and instrumented section 10 could be jointed to each other, and to the production piping 7, by threaded or welded connections. Alternatively, these components could be incorporated into a single section of piping that was joined to the production piping 7 or they could be inserted directly into inside diameter of the production piping 7 itself.

When laser light is used, a filter, such as a dielectric filter (not shown), may be incorporated at the probe to filter out emission lines around the laser wavelength so as to eliminate the effect of glass Raman scattering.

2. Fiber Optic Cables

Each sensor 12 is optically connected to a light source 16 and a remote fluid analyzer 6 by a fiber optic cable 13 containing a pair of optical fibers 14' and 14". Preferably, the optical fibers, which may comprise a bundle of optical fibers, are of the multimode type. The first optical fiber 14' is coupled to a light source 16, which is preferably located at a remote location, such as the surface. The second optical fiber 14" is coupled to a fluid analyzer 6, which is also preferably located a remote location, such at the surface. Thus, the fiber optic cable 13 transmits light from the light source 16 to the sensor 12 and transmits light from the sensor to the fluid analyzer 6.

3. Light Source

When used in connection with the attenuation method, a broadband light source 16 should be used, such as a quartz tungsten halogen lamp. Preferably, the light source 16 emits light having wavelengths sufficiently broad to encompass the major absorption peaks of the constituents whose concentration is to be determined, as previously discussed. In the case of mixtures of oil, water and/or natural gas, the wavelength of the light should encompass the ranges previously discussed in section I.

When used in connection with the fluorescence method, the light source 16 should be an extremely narrow band source, and preferably be a monochromatic light source, such as a diode laser or a diode-pumped solid state (DPSS) laser. When used in circumstances requiring transmission of light over long distances, the light source 16 emits light having a wavelength in the ranges previously discussed in section II.

4. Fluid Analyzer

As shown in FIG. 1, the fluid analyzer 6 comprises a spectrographic detector 18, a computer 20, and an indicator 22. The spectrographic detector 18 includes a spectrograph for dispersing the light from the collection fiber into its component wavelengths and a detector for sensing the intensity at each of these wavelengths.

Depending on the analysis technique to be utilized, the detector may comprise an InGaAs diode array to detect the intensity at each of the dispersed wavelengths. Such an array typically has a spectral sensitivity from 900 nm to 1700 nm. The primary advantage of using an array for detection is its ability to detect the light intensity simultaneously at every detected wavelength. For scanning systems, whether of interferometric or grating type, each wavelength's intensity is detected at a different discrete time. Since downhole scattering is a temporal phenomenon, this would make the measured effect of the scattering appear to be wavelength dependent. With the use of a diode array, the simultaneous detection of intensity at all detected wavelengths ensures that the effects of scattering are common to all wavelengths and facilitates the use of a normalization method to correct for scattering.

Alternatively, in connection with fluorescence analysis methods, a charge coupled device silicon array may be used for the detector. As a further alternative when using the fluorescence method, a filter or beam splitter can be used to direct the collected laser signal to one detector while the fluorescent signal is directed to a second detector. In this case, the detectors can be single element detectors that effectively integrate the signal intensities for all of the impinging wavelengths. The output of the detector for the laser signal is proportional to the integrated laser intensity and the output of the detector for the fluorescent signal is proportional to the integrated fluorescent signal. Normalization can be performed by taking the ratio of the two detector outputs in either analog or digital form.

Regardless of the type of detector used, the computer 20 is programmed with software that allows it to read the array of intensities from the spectrographic detector 18.

Regardless of whether the attenuation or the fluorescence analysis technique is used, in operation, the output of the light source 16 is directed into the proximal end of the first fiber optic 14' located at the surface, as shown in FIG. 1. The fiber optic 14' permits the transmission of the light downhole to the remote sensor 12. The sampling portion of the remote sensor 12 is in contact with the downhole fluid stream 3 that is to be analyzed. After exiting the fiber optic 14', the source light interacts with the fluid 3, as shown in FIG. 3, causing the fluid to absorb, scatter, transmit and/or fluoresce light. Subsequently, the second fiber optic 14" collects a portion of the light which is emerging from the fluid stream 3 (which may include scattered light from the source, transmitted light, and fluorescent radiation) and transmits this light to the surface, where its intensity is detected as a function of wavelength using the spectrographic detector 18. The data from the spectrographic detector 18 is then input into the computer 20.

The computer 20 is programmed with software containing an algorithm that determines the composition of the fluid 3—that is, the concentrations of predetermined constituents, for example, the percentages of oil and water—based on the intensity of the light emerging from the fluid at one or more selected discrete wavelength or range of wavelengths, as determined by the spectrographic detector 18. These concentrations are indicated on the indicator 22, which may be a digital readout device.

Figure 4:
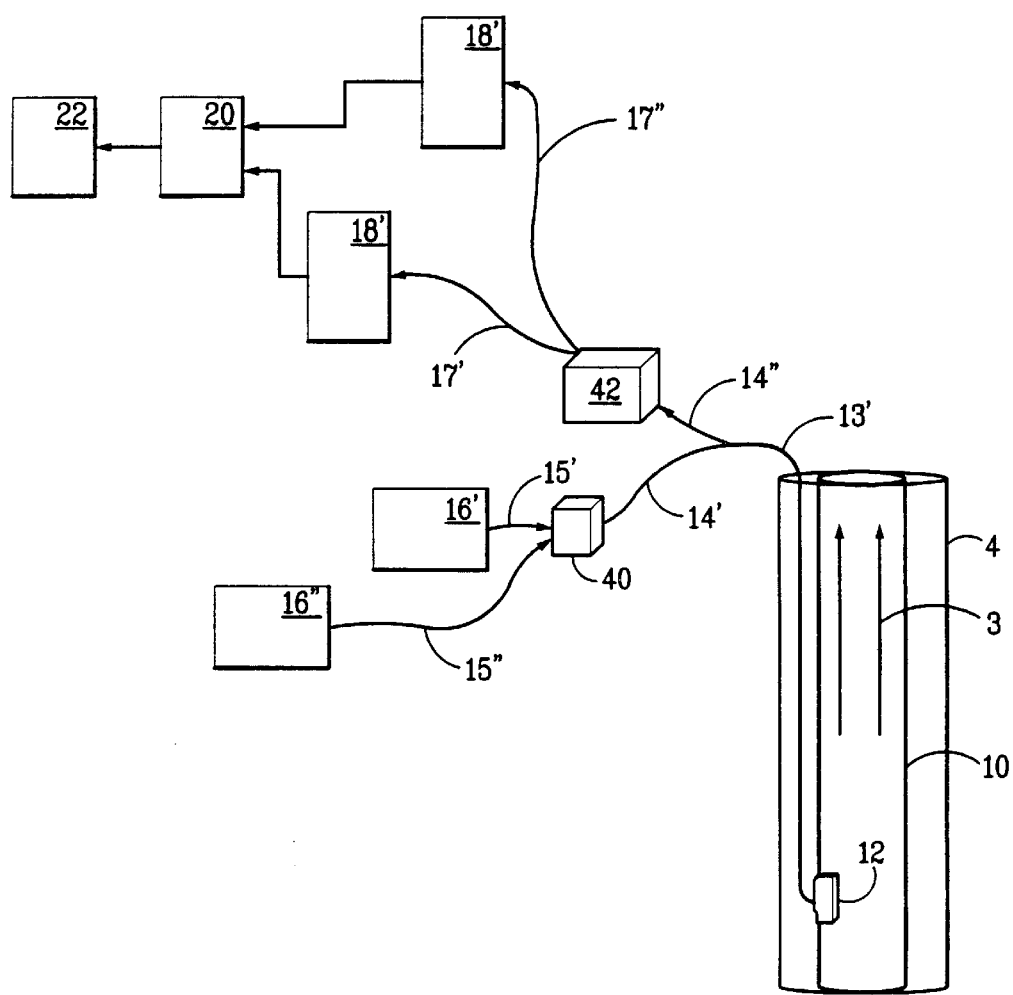
FIG. 4 is schematic diagram of an alternate embodiment of the fluid analysis system according to the current invention installed in a section of pipe.

An apparatus for simultaneously employing both the fluorescence and attenuation methods of analysis is shown in FIG. 4. In this case. two separate light sources 16' and 16" and two separate spectrographic detectors 18' and 18" are utilized. The first light source 16' is used for the fluorescence portion of the analysis and, as discussed above, preferably generates monochromatic light. The second light source 16" is used for the attenuation portion of the analysis and, as discussed above, preferably generates broad band light. The first spectrographic detector 18' is used for the fluorescence analysis and, as discussed above, preferably comprises a diode array. The second spectrographic detector 18" is used for fluorescence analysis and, as discussed above, preferably comprises a charged couple device.

Light from the two sources 16' and 16" may be directed by optic fibers 15' and 15" into a common optic fiber 14' by using a beam combining device 40. The beam combining device 40 may consist of a dichromatic beam splitter, a fiber optic coupler, a fiber optic multiplexer, or a similar type of device. Light from both light sources 16' and 16" is carried downhole by the common fiber optic 14' to a common sensor 12, such as that previously discussed. After interaction of light from both sources 16' and 16" with the fluid stream 3, light from the fluid stream is collected and returned to the surface by a common carrier fiber optic 14" . Light exiting from the fiber 14" is split into two signals of having light in two different wavelength ranges by a splitter device 42, which may be a filter, a filter set, a beam splitter, a fiber optic splitter, a fiber optic demultiplexer, a grating, or a similar device.

One signal comprises light in the wavelength range that incorporates the wavelengths of the first, monochromatic light source 16' and the wavelengths of the fluorescence that was generated downhole by the interaction of light from the monochromatic source and the fluid stream 3. This signal is directed to the first spectrographic detector 18' by means of fiber optic 17'. The second signal comprises the wavelength range that incorporates the wavelengths of the second, broadband source light source 16" . This signal is directed to the second spectrographic detector 18" by means of fiber optic 17". The processing of these independent signals is performed by the computer 20 using the software and algorithms of the current invention, as discussed further below—specifically, a first algorithm developed from an attenuation-based calibration would be used to determine concentration based on the attenuation analysis and a second algorithm developed from a fluorescence-based calibration would be used to determine concentration based on the fluorescence analysis. The concentration resulting from the two methods of analysis could then be compared for verification.

B. Algorithms/Software

Figure 15:
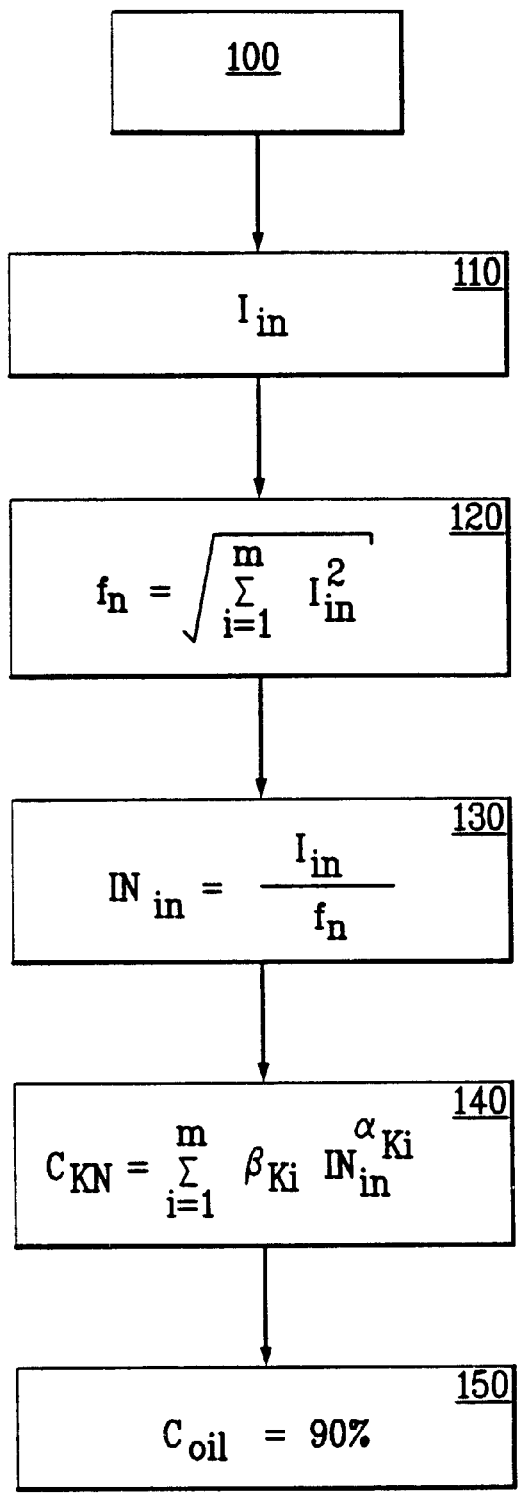
FIG. 15 is a schematic diagram showing the software programed into the computer portion of the fluid analyzer shown in FIG. 1.

Using techniques well known in the art, the computer 20 is programed with software, shown schematically in FIG. 15, for determining the concentration based on the light components measured by the spectrographic detector 18. As shown in FIG. 15, in operation, in the first step 100, the computer 20 first directs the light source 16 to transmit a beam of light to the sensor 12, which directs the light emerging from the fluid to the spectrographic detector 18. In the second step 110, the computer directs the spectrographic detector 18 to determine the intensity of the components of the emerging light at wavelengths within a predetermined range. In step 120, the normalization factor $f_n$ is calculated from the measured intensities, for example using the equation indicated. In step 130, the measured intensities at selected wavelengths, preprogramed into the computer, are normalized using the normalization factor determined in step 120. In step 140, the normalized intensities are applied to one or more algorithms preprogramed into the computer so as to calculate the concentration of the constituents of interest. In step 150, the calculated concentration, for example 90% oil, is displayed on the indicator 22. The normalization techniques applied in steps 120 and 130 and the algorithm applied in step 140 are discussed in detail below.

As previously discussed, according to an important aspect of the current invention, the measured intensities of the light emerging from the fluid are normalized to eliminate the effect of scattering on the analysis. When a light attenuation method is used, normalization is preferably performed using a characteristic of the intensity of the light emerging from the fluid over a range of wavelengths. Preferably, the vector length of the emerging light spectrum is used. Mathematically, the vector length is represented as:

$$f_n = \sqrt{\sum_{i=1}^{m} I_{in}^2} \quad [1]$$

where:
- n=a number representing the particular mixture being analyzed,
- i=represents discrete wavelengths or wavelength ranges,
- $I_{in}$=the measured intensity of the component of the emerging light for mixture n existing at wavelength i,
- $f_n$=the vector length for mixture n,
- m=the total number of component intensities used in the normalization (e.g., the total number of component intensities measured over a predetermined wavelength range).

Note that for purposes of the current invention, preferably, the measured intensity $I_{in}$ at any given wavelength is determined by integrating the intensity over at least a small wavelength band about the given wavelength in order to minimize errors due to slight deviations in wavelength detection. Thus, for example, the measured intensity at a wavelength of 1100 nm, $I_{1100}$, is determined by integrating the intensity over a wavelength band from 1095 nm to 1105 nm. Alternatively, the integrated intensity over a relatively large band of wavelengths (e.g., 950 to 1000 nm ) could be used if such a band contained valuable information on the concentration of a particular constituent.

Normalization is performed by dividing the measured intensity $I_{in}$ in at each wavelength in the $n^{th}$ spectrum by the vector length $f_n$ so that $$IN_{in} = IN_{in}/f_n \quad [2]$$

Where $IN_{in}$=the normalized intensity of mixture n at wavelength i.

Although vector normalization is a preferred method, those knowledgeable in the art will recognize that other normalization routines may be used. For example the spectral data can be normalized to the area of the spectrum:

$$f_n = \sum_{i=1}^{m} |I_{in}| \quad [3]$$

or to the intensity at a specific wavelength, or to the integrated intensity across one or more spectral regions.

Note that, according to the current invention, when using the attenuation method, it is not necessary (although it is not prohibited) to normalize the measured intensities to the spectrum of the light from the light source 16 that is directed to the fluid. This is due to the fact that changes in light source intensity at the surface are expected to be relatively wavelength independent and thus will not effect the analysis according to the current invention, in which only the relative intensities, not the absolute magnitudes, are used.

When using the fluorescence method, normalization is performed by reference to the intensity of the portion of the collected light that represents the scattered laser light, determined by detecting the intensity of the collected light in a small band of wavelengths around the wavelength of the laser. For example, the measured intensities can be normalized by dividing the intensity of the fluorescent radiation at each wavelength $I_i$ by the intensity of the transmitted laser light IL (e.g., determined by measuring the intensity of the transmitted light component at the wavelength of the laser light) so that:

$$IN_{in} = I_{in}/IL \quad [4]$$

Other laser light intensity related values could also be used for the normalization, such as the area under the transmitted laser light spectrum.

Regardless of whether the attenuation or fluorescence methods of analysis are used and regardless of which normalization technique is used, the concentration of each constituent of interest is preferably determined from an equation of the type:

$$C_{kn} = \sum_{i=1}^{m} \beta_{ki} IN_{in}^{\alpha_{ki}} + b_k \quad [5]$$

where:
- k=A number representing the particular constituent of interest (for example, 1=oil, 2=water, and 3=gas)
- $C_{kn}$=The concentration of constituent k for mixture n (for example, $C_{12}$ is the percentage of oil for mixture 2).

n=A number representing the particular fluid that is the subject of the analysis (for example, n=1 represents a fluid flowing in an oil well that consists of a mixture of 10% water and 90% oil, n=2 represents the well fluid at a later point in time, when its relative constituents may have changed).

i=A number representing the selected key wavelengths (for example, 1=1000 nm (or 950 to 1050 nm), 2=1110 nm (or 950 to 1050 nm), etc.).

m=The total number of light components whose intensities are used in the algorithm, which may, but need not be, the same as the number of light component intensities used in calculating the vector length or other normalization factor.

$\beta_{ki}$=The weighting factor for constituent k at each of the selected wavelengths or wavelength ranges i, discussed further below.

$IN_{in}$=The normalized intensity of the component of the light at wavelength i for fluid mixture n determined as discussed above.

$\alpha_{ki}$=Exponents for constituent k at each of the selected wavelengths or wavelength ranges i. Preferably, $\alpha$ is 1 so that the algorithm will be linear. However, in some circumstances, linearity may not yield sufficient accuracy, in which cases $\alpha$ may have values other than 1. Moreover, all of the $\alpha_i$ values may not be the same. For example, $\alpha_1=2$, $\alpha_2=\frac{1}{2}$, etc.

$b_k$=A constant.

Essentially, the weighting factor $\beta_{ki}$ for each constituent shows the relative weight to be given the intensity at each of the selected wavelengths in determining the concentration of that constituent—that is, the extent to which the intensity of the light component at a given wavelength is a predictor of the concentration of the constituent of interest. The larger the variation in the intensity of the component of the emerging light at a given wavelength as the concentration of a particular constituent varies, relative to the intensity variation at that wavelength as the concentration of other constituents varies, the larger the weighting factor $\beta_{ki}$ for that particular constituent at that wavelength. The weighting factors may be positive or negative. If all of the wavelengths are used, rather than only the most significant, then. some of the weighting factors may be zero.

In any event, the normalized intensity of the light component at each wavelength to be used in the algorithm is multiplied by a weighting factor the value of which is dependent upon the wavelength. The normalized and weighted intensities are then summed to arrive at the concentration of the constituent for which the algorithm was developed.

For the sake of illustration, consider a highly-simplified example of fluid flowing downhole in a well in which the concentration of three constituents—oil, water, and gas—are to be determined using linear algorithms based on the normalized light component intensities at five selected wavelengths (m=5) from a set of five wavelengths—1100, 1200, 1300, 1400, and 1500 nm. Further suppose that, as a result of the application of a regression technique to a set of calibration data, discussed further below, values for the weighting factors $\beta$ at each wavelength were determined for the three constituents as follows:

| Wavelength (i) | Weighting Factors ($\beta$) | | |
|---|---|---|---|
| | Oil | Water | Gas |
| 1100 | 100 | 400 | 200 |
| 1200 | 250 | 400 | 0 |
| 1300 | 130 | 100 | 80 |
| 1400 | 0 | 225 | 30 |
| 1500 | 150 | 0 | 20 |

Equation 5 would then result in the following algorithms for concentrations of oil, water, and gas:

$C_{oil}$=100 $IN_{1100}$+250 $IN_{1200}$+130 $IN_{1300}$+0$IN_{1400}$+150 $IN_{1500}$  [5a]

$C_{water}$=400 $IN_{1100}$+400 $IN_{1200}$+100 $IN_{1300}$+225 $IN_{1400}$+0 $IN_{1500}$ [5b]

$C_{gas}$=200 $IN_{1100}$+0 $IN_{1200}$+80 $IN_{1300}$+30 $IN_{1400}$+20 $IN_{1500}$  [5c]

For the sake of simplicity, all of the wavelengths used for the three equations above were drawn from the same five wavelength set. However, in actual practice, the selected wavelengths for each constituent might come from completely different sets of wavelengths. However, generally, all of the wavelengths used in each of the algorithms would fall within the same range of wavelengths. For example, when using a method based on the attenuation of near-IR light or the inducement of fluorescence caused by near-IR light, the wavelengths used in the algorithm would all fall somewhere within the near-IR range (e.g., in the range from 800 nm to 1600 nm).

Although only five wavelengths were used in the algorithms in the example above, in practice, a greater number of wavelengths may often be used. For example, the algorithm might contain each wavelength in the 1100 to 1500 nm range—that is, four hundred wavelengths (m=400)—so that there were four hundred weighting factors, each of which is applied to the component of the normalized intensity at the respective wavelength. Alternatively, in the limit, an algorithm utilizing only a single wavelength could also be used—example, $C_{oil}$=200 $IN_{1300}$+12—provided that it yielded sufficient accuracy for the particular application.

In any event, during operation, the intensity of the light components at the prescribed wavelengths of the light emerging from the fluid flowing in the well is measured using either an attenuation or fluorescence technique. These measured component intensities are then normalized, as discussed above. For example, if vector length normalization were used, the vector length of the spectrum over a range of wavelengths (for example, all of the wavelengths in the 1100 to 1500 nm range) would be calculated from the measured intensities and the measured intensity at each of the wavelengths used in the algorithm would then be divided by the vector length so as to arrive at normalized intensities for those wavelengths. For example, a set of normalized intensities might be:

| Wavelength (i) | Normalized Intensity (IN) |
|---|---|
| 1100 | .06 |
| 1200 | .04 |
| 1300 | .05 |
| 1400 | .03 |
| 1500 | .02 |

Substituting these normalized intensities into equations 5a, 5b and 5c would yield concentrations of 52% oil, 26% water, and 17% gas.

In some applications, the algorithm might involve two or more equations for each constituent, each covering a different concentration range—for example, one equation for oil concentrations between 0% and 50% and another equation, with different weighting factors and/or selected wavelengths, for oil concentrations between 50% and 100%, etc.

When using several algorithms covering different ranges for the same constituent, it is desirable to identify into which subset range of concentrations a particular mixture being measured belongs before choosing the algorithm to determine the concentration. Thus, an algorithm generated for concentrations over the entire 0 to 100% concentration range could be used to preliminarily screen the data and, based on the concentration calculated using that algorithm, a more accurate, narrower range algorithm could be used for the final calculation. Alternatively, a Soft Independent Modeling by Class Analogy (SIMCA) could be used. In this method, a classification model is generated based on the light intensities of mixtures that fall into the different concentration ranges selected. The model is then used to predict into which concentration range an unknown mixture falls. Once a mixture has been assigned to a certain subset range of concentrations, a calibration algorithm optimized for that range can be used to more accurately determine the concentration of the constituents of interest. One knowledgeable in the art will realize that classification models other than SIMCA can be used to achieve the same goal, such as K-nearest neighbors, discriminate analysis, principal component analysis, and neural nets.

In addition to the software for calculating concentrations, the computer 20 may also be programmed with software for performing the calculations associated with the development of the specific algorithm from the calibration data—that is, the identification of the weighting factors used to weight the importance of the intensities at various wavelengths in determining concentration, as discussed further below.

IV. Development of the Concentration Algorithm

A. Equipment

The specific form of the algorithm discussed above and shown as equation is developed for each constituent by identifying a range of wavelengths that encompasses those wavelengths whose intensities are likely to provide the maximum information about the concentration of that constituent, determining the weighting factors $\beta_{ik}$ associated with each of the wavelengths in the range, and selecting those wavelengths to be used in the algorithm based on the weighting factors. This is done by performing a calibration for the particular type of fluid to be analyzed—for example, the fluid from the well into which the sensor 12 will be installed—and the particular constituents for which concentration is to be determined—for example, the particular type of crude oil being produced by the well.

Figure 5:
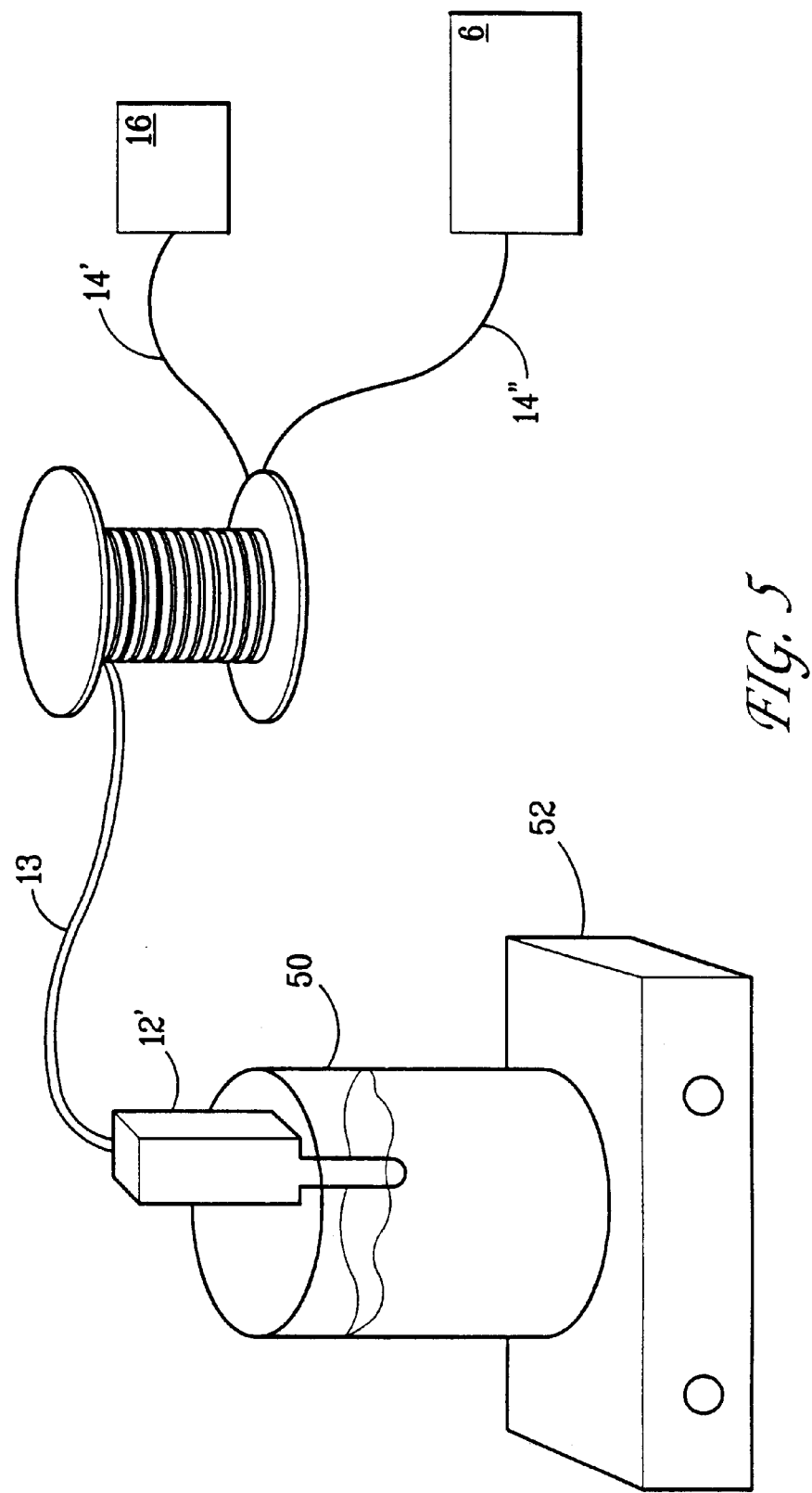
FIG. 5 is schematic diagram of the equipment for performing a calibration according to the current invention.

Calibration is performed by obtaining quantities of each constituent and preparing various mixtures of differing concentrations that preferably span the range of concentrations to be encountered in operation. For example, if a mixture of crude oil and water from a producing well is to be analyzed, a quantity of pure crude oil extracted from the fluid produced by the well is obtained. The sensor 12 is then installed onto a container 50, as shown in FIG. 5. A stirring device, such as a stir plate 52, is used to mix the oil and water in the container 50. The sensor 12', which may be similar to the sensor 12 shown in FIGS. 2 and 3, is coupled to the fluid analyzer 6 and light source 16 using a fiber optic cable 13. The light source 16 and fluid analyzer 6 are as discussed above in connection with FIG. 1. Preferably, the same type and length of fiber optic cable 13 that will be used in actual service is employed so as to remove the effects of attenuation of the light as it travels through the long fiber optic cable on the calibration results.

B. Acquisition And Normalization of Calibration Intensities

1. Experiment 1—Oil Concentration Using Attenuation

Figure 6:
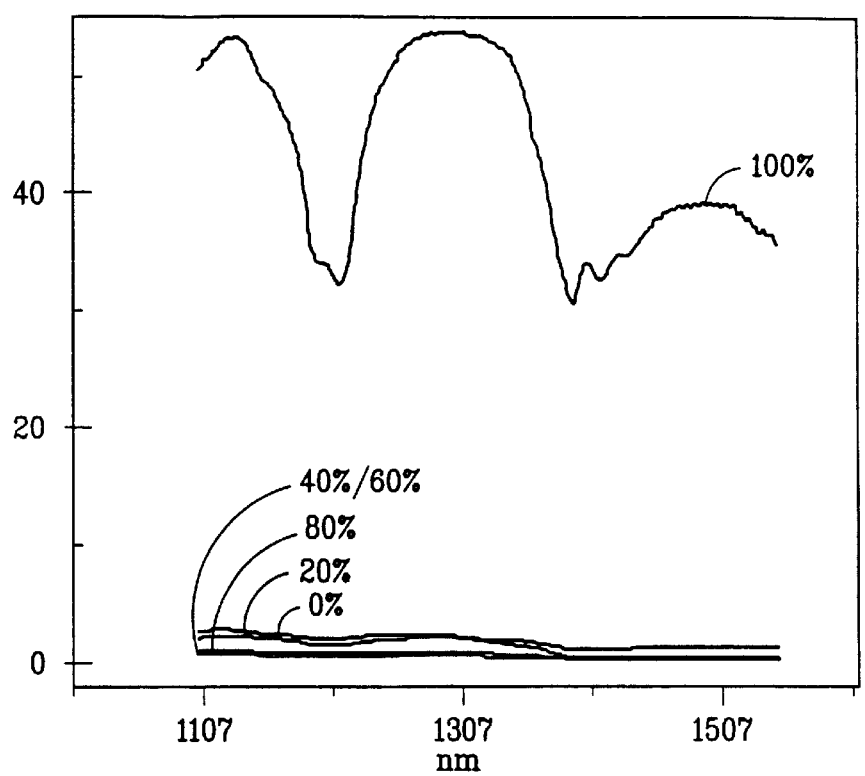
FIG. 6 is a plot of measured light intensity versus wavelength for oil/water mixtures ranging from 0 to 100% oil using the near-IR attenuation method. The X-axis is the light wavelength in nanometers. The Y-axis is the instrument's response in analog to digital converter counts.
Figure 7:
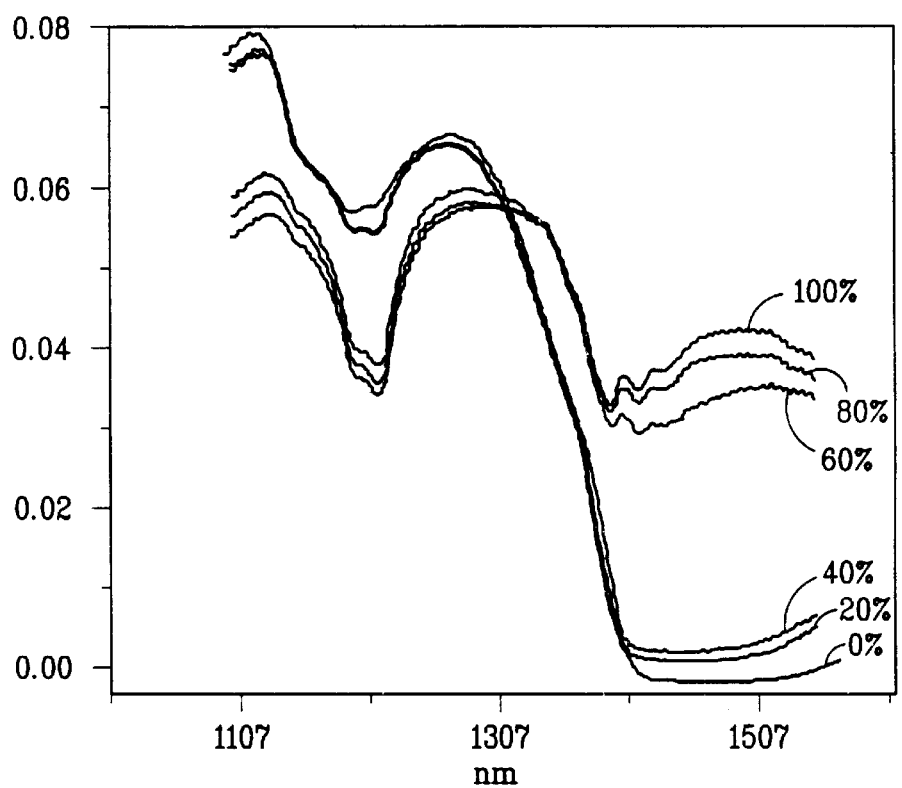
FIG. 7 is a plot of normalized light intensity versus wavelength based on the data shown in FIG. 6. The X-axis is the light wavelength in nanometers. The Y-axis is the instrument's response in analog to digital converter counts.

The method for acquiring and normalizing the component light intensities to be used in developing the details of the concentration algorithm will now be discussed by way of example—specifically, an experiment that was conducted using the near-IR attenuation method, portions of the spectra resulting from this method are shown in FIGS. 6 and 7.

The equipment set up used is shown in FIG. 5. Initially, the container 50 was filled with pure crude oil. In actual practice, the crude oil would be extracted from the fluid produced by the well. For purposes of this experiment, light Pennsylvania crude oil was used. The light source 16 used for this experiment was a quartz tungsten halogen lamp, which generated light having wavelengths that encompass the 1100 nm to 1550 nm range. The intensity of the source was set just below saturation of the detector at 0.1 sec integration (~50,000 counts/sec). This light was directed by the fiber optic 14' to the sensor 12, which then directed it to the oil in the container 50. The light emerging from the oil was collected by the sensor 12 and transmitted by fiber optic 14" to the fluid analyzer 6.

The fiber optics 14' and 14" were each approximately nine feet long. The fluid analyzer 6 employed a diode array to measure the intensity of the emerging light versus its wavelength so as to essentially develop the spectrum of light emerging from pure oil of the type produced by the well. This data was then stored in the computer 20. Since crude oil has absorption peaks at about 1200 nm and 1400 nm, it was determined that the range of wavelengths to be used in the calibration was 1100 nm to 1520 nm. The spectrum of light emerging from pure crude oil in this wavelength range is shown in FIG. 6. Since the intensity of the light emerging from the fluid is reduced at those wavelengths at which appreciable absorption occurs, the areas of greatest absorption appear as troughs in the spectrum of the emerging light. Thus, the spectra shown in FIG. 6 and utilized according to the current invention are not the spectra of the absorbed light but rather the spectra of the emerging light from the fluid, which contains those portions of the light that are scattered by or transmitted through the fluid (i.e., not absorbed).

Next, water was added in carefully titrated increments to the container 52 and additional spectra were obtained and stored in the computer until spectra were acquired over a range of crude oil concentrations down to 50%. This procedure was repeated starting with a container of pure water and adding oil in carefully titrated increments until spectra were acquired over a range of water concentrations down to 50%. In this experiment, spectra where obtained at a total of thirty eight different concentrations spanning 0% to 100% oil concentrations. For simplicity, eleven of these spectra (i.e., in 10% increments) are shown in FIG. 6 over wavelengths in the approximately 1100 nm to 1550 nm range. As discussed below, in actual practice, the number of spectra used for the calibration may depend on the regression technique utilized during the calibration calculations.

In this experiment, the stir plate 52 was used to maintain good mixing of the oil and water. In actual practice, the degree of mixing during data acquisition should approximate that of the fluid to be encountered in actual service— for example, the degree of mixing associated with the fluid flowing down hole in the well.

At each concentration, a spectrum for the 1100 nm to 1550 nm range was obtained by measuring the intensity of the light component at each wavelength within the range so that intensity was measured at a total of 450 wavelengths. The intensity of the light from the fluid was measured simultaneously at all wavelength over a 0.1 second period. This measurement was repeated one hundred times and the readings averaged to arrive at a final intensity value for each wavelength. Data acquisition was repeated ten times so that ten sets of data was obtained for each mixture.

As can be seen in FIG. 6, the absolute intensity of the spectra vary quite dramatically with concentration. Specifically, higher concentrations of oil yield low absolute spectral intensities at the wavelengths for which absorption is high. As previously discussed, this results from two phenomena associated with the presence of oil—increased scattering and increased near-IR absorption. However, as also previously discussed, whereas the amount of absorption is a function of only the concentration of oil, the amount of scattering depends upon both the concentration and various multiphase characteristics, such as droplet size. Therefore, according to an important aspect of the current invention, the effect of scattering is minimized by normalizing the spectra. Thus, using the method previously discussed, the vector length of each of the spectra in FIG. 6 was calculated. Each spectrum was then divided by its own vector length so as to generate the normalized spectra shown in FIG. 7. As can be seen, the peak intensity trends follow concentration, indicating that the normalized spectra are independent of the scattering properties of the various mixtures.

Based upon the normalized spectra shown in FIG. 7, the weighting factors $\beta$ for each wavelength in the 1100 nm to 1550 nm range were determined (a total of 450 weighting factors) using a partial least squares regression technique, discussed below. Based on these weighting factors, an algorithm was developed in the form of equation 5 (linear, with $\alpha=1$) for the calculation of the concentration of oil, $C_{oil}$, in mixture n based on normalized intensity IN a each wavelength in the 1100 nm to 1520 nm range:

$$C_{oil,n} = \beta_{oil,1100\ nm} IN_{n,1100\ nm} + \beta_{oil,1101\ nm} IN_{n,1101\ nm} + \ldots + \beta_{oil,1520\ nm} IN_{n,1520\ nm} \quad [6]$$

Figure 8:
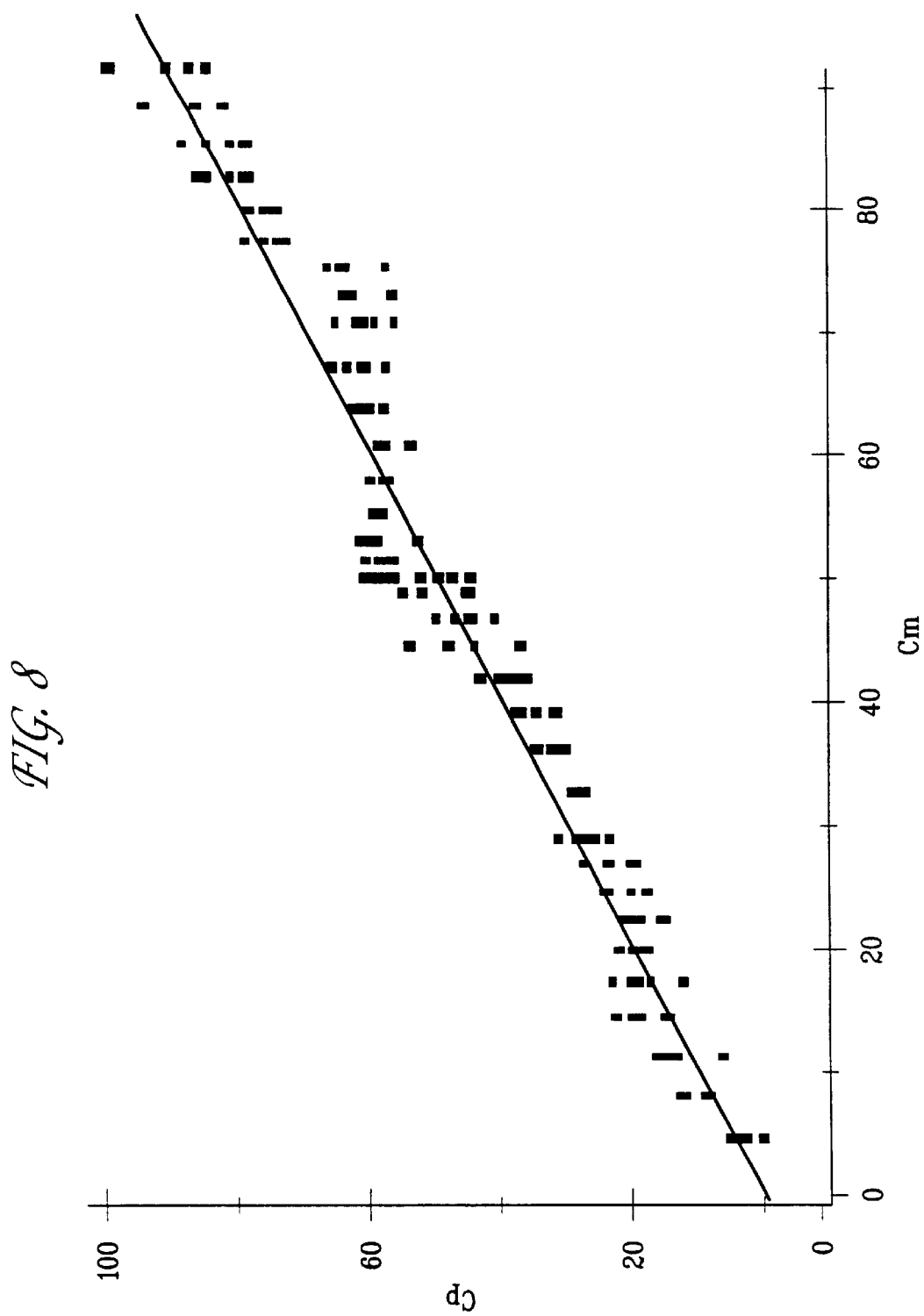
FIG. 8 is a plot of predicted concentration $C_p$ versus measured concentration $C_m$ for oil using an algorithm according to the current invention based on the data shown in FIG. 6.

A leave one out validation technique was employed to check the accuracy of the algorithm. Specifically, the partial least squares regression was run for each mixture used in the calibration except one and the resulting algorithm was then used to calculate the concentration of oil in the mixture left out and this computed value was compared to the actual value. This procedure was repeated for each mixture used in the calibration and the predicted versus actual values are shown plotted in FIG. 8. These data revealed a standard error for the algorithm of only 2.9% in the percentage concentration value.

2. Experiment 2—Oil Concentration Using Fluorescence

Figure 9:
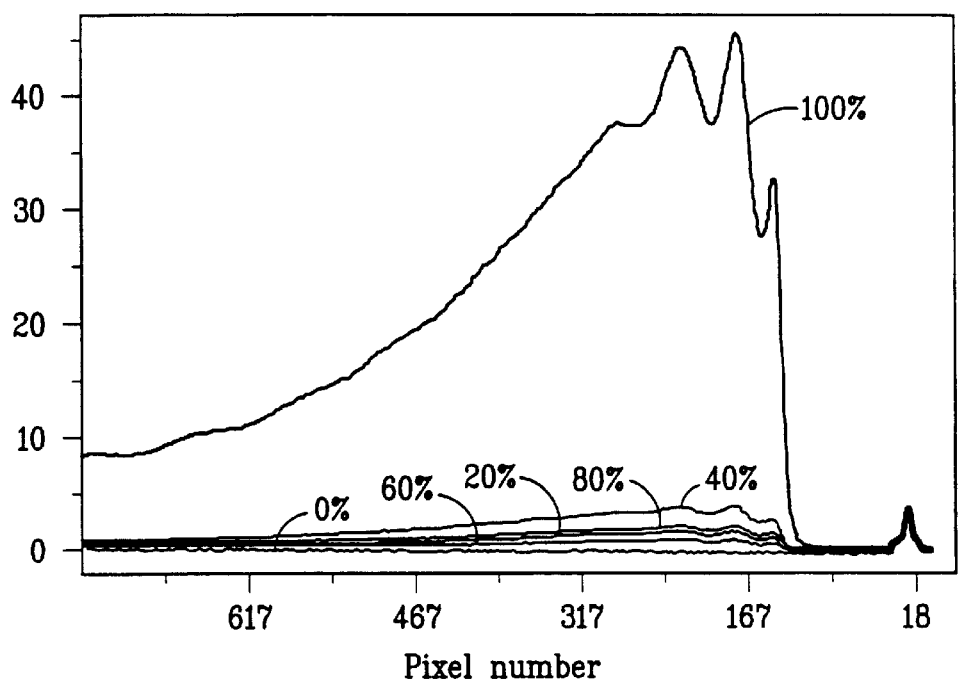
FIG. 9 is a plot of measured light intensity versus wavelength for oil/water mixtures ranging from 0 to 100% oil using the near-IR fluorescence method. The X-axis is the wavelength in Pixel number. The Y-axis is the instrument's response in arbitrary units.

The calibration procedure described above, as well as the procedure for determining weighting factors at each wavelength, as discussed below, are essentially the same whether the absorption or fluorescence methods are used to generate the emerging light from the fluid. Thus, a second experiment was conduced using the near-IR fluorescence method. The equipment used in this experiment was the same as that shown in FIG. 5 and discussed above in connection with the near-IR attenuation experiment, except in this case, the light source 16 was DBR laser, which emitted monochromatic light at a wavelength of about 852 nm, and a CCD was used for the spectrograph detector 18. The same ratios of oil/water concentrations were used to generate the spectra based on near-IR attenuation shown in FIG. 6 were used and the intensities were measured using a similar procedure. Data was acquired for each mixture five times. In this case, the intensity was determined at each pixel in about the 18 to 770 pixel range (corresponding to approximately 850 nm to 1300 nm). The resulting raw spectra ranges are shown in FIG. 9. The scattered laser light is clearly visible at a pixel number slightly greater than 18. The measured intensity at each wavelength was then normalized by dividing it by the peak amplitude of the scattered laser light so as to obtain the normalized spectra shown in FIG. 10.

Figure 10:
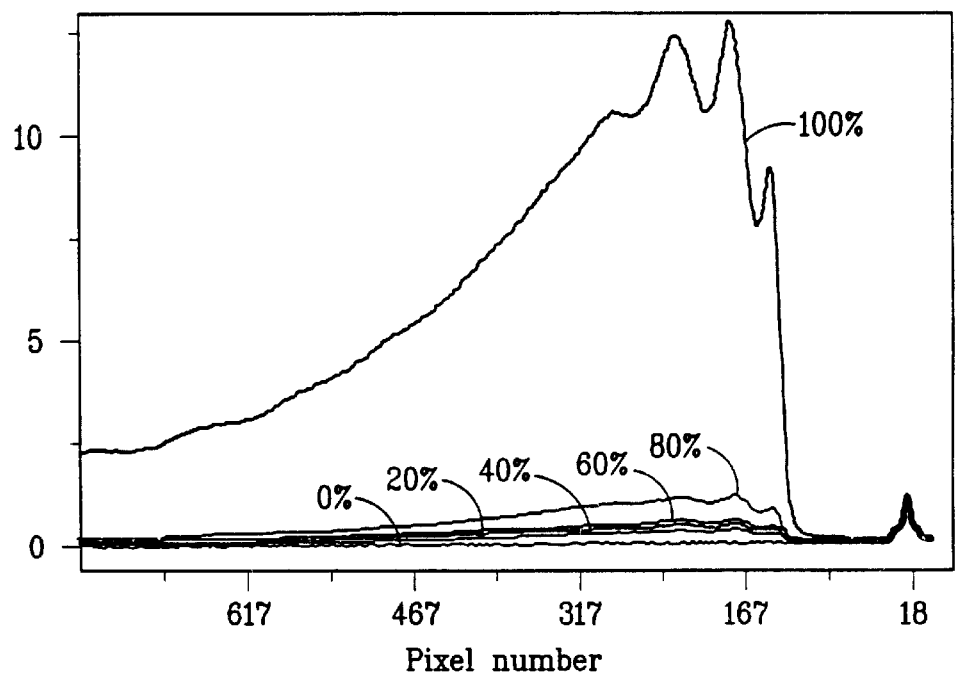
FIG. 10 is a plot of normalized light intensity versus wavelength based on the data shown in FIG. 9. The X-axis is the wavelength in Pixel number. The Y-axis is the response in arbitrary units.

Based upon the normalized spectra shown in FIG. 10, the weighting factors $\beta$ for each pixel in the 18 to 770 pixel range were determined (a total of 752 weighting factors) using a partial least squares regression technique, discussed below. Based on these weighting factors, an algorithm was developed in the form of equation 5 (linear, with $\alpha=1$) for the calculation of the concentration of oil, $C_{oil}$, in mixture n based on normalized intensity IN a each wavelength in the 18 to 770 pixel range:

$$C_{oil,n} = \beta_{oil,18} IN_{n,18} + \beta_{oil,19} IN_{n,19} + \ldots + \beta_{oil,770} IN_{n,770} \quad [7]$$

A leave one out analysis revealed a standard error for this algorithm of 5.6%. The oil concentrations predicted by the near-IR fluorescence algorithm are shown graphed versus the actual concentration values in FIG. 11.

3. Experiment 3—Gas Concentration Using Attenuation Method

Figure 11:
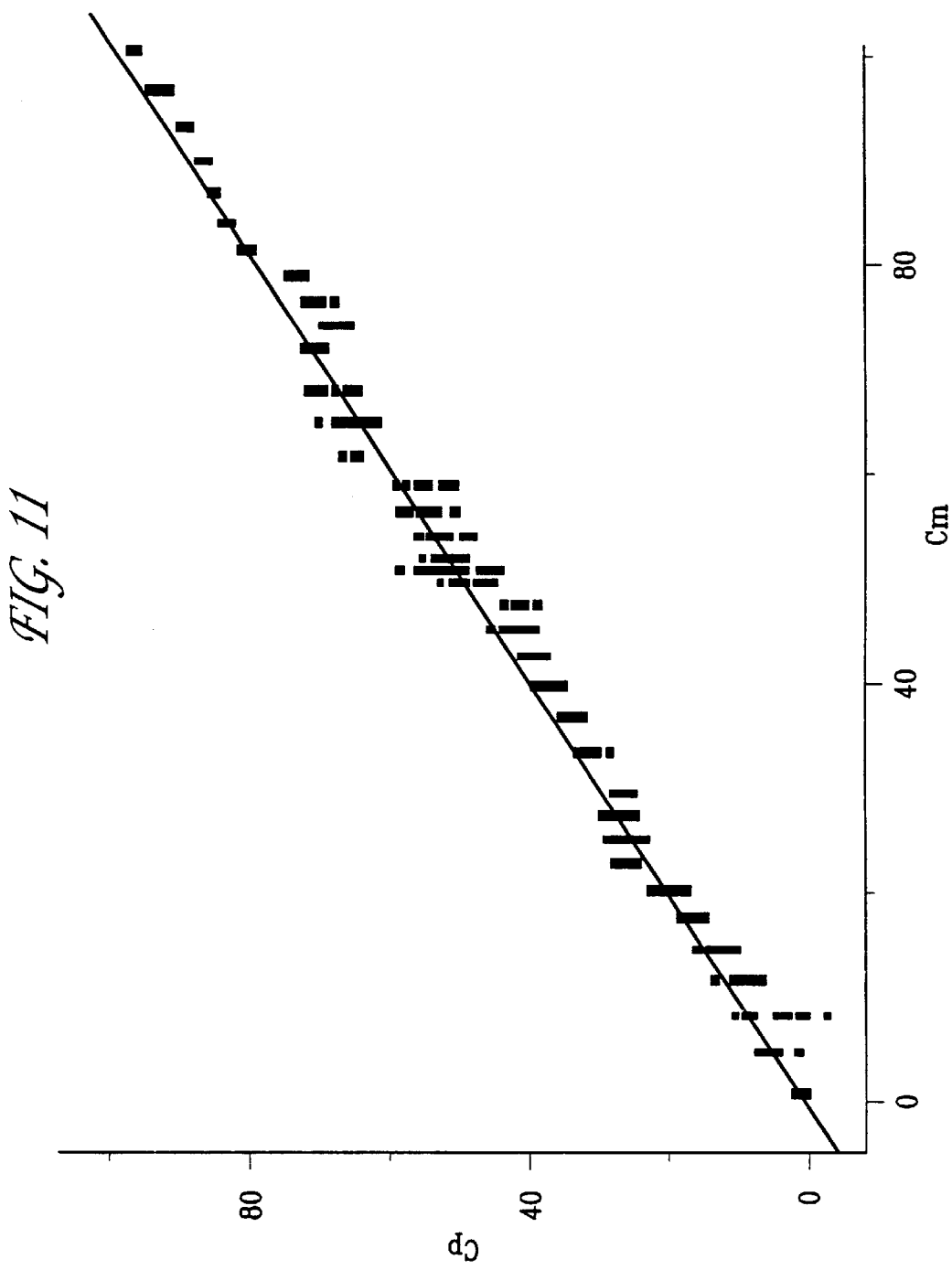
FIG. 11 is a plot of predicted concentration $C_p$ versus measured concentration $C_m$ for oil using an algorithm according to the current invention based on the data shown in FIG. 9.

The attenuation method of the current invention can also be used to determine the concentration of natural gas in a fluid flow. A simulation of natural gas dissolved in crude oil, or a crude oil/water mixture, was performed using isooctane (2,2,4-trimethylpentane) as a proxy for the natural gas. Natural gas consists mainly of methane ($CH_4$), ethane ($C_2H_6$) and other small chain hydrocarbons (e.g., propane and butane), which are characterized by the presence of methyl groups (—$CH_3$). Isooctane has a high percentage of methyl groups and its addition to crude oil flow would closely mimic the near-IR absorption behavior of an addition of liquefied or dissolved natural gas. The temperatures and pressures that exist downhole would generally cause natural gas to be in a liquid state. Crude oil consists several different lengths of chain hydrocarbons, which consist of some methyl groups ($CH_3$) but predominantly methylene groups ($CH_2$). Both groups have distinct absorption bands in the near-IR region. Evans et. al, Analytical Chemistry, vol. 23, no. 11 (1951) used the ratio of these two absorption bands to determine the number of methyl and methylene groups per molecule in paraffins and lubrication oils. FIG. 11 shows near-IR spectra of crude oil with varying amounts of isooctane (0–50%). As the isooctane concentration increases, the methyl spectral band grows in intensity relative to the methylene band, which allows the method described above to distinguish between the two organic fluids.

Figure 14:
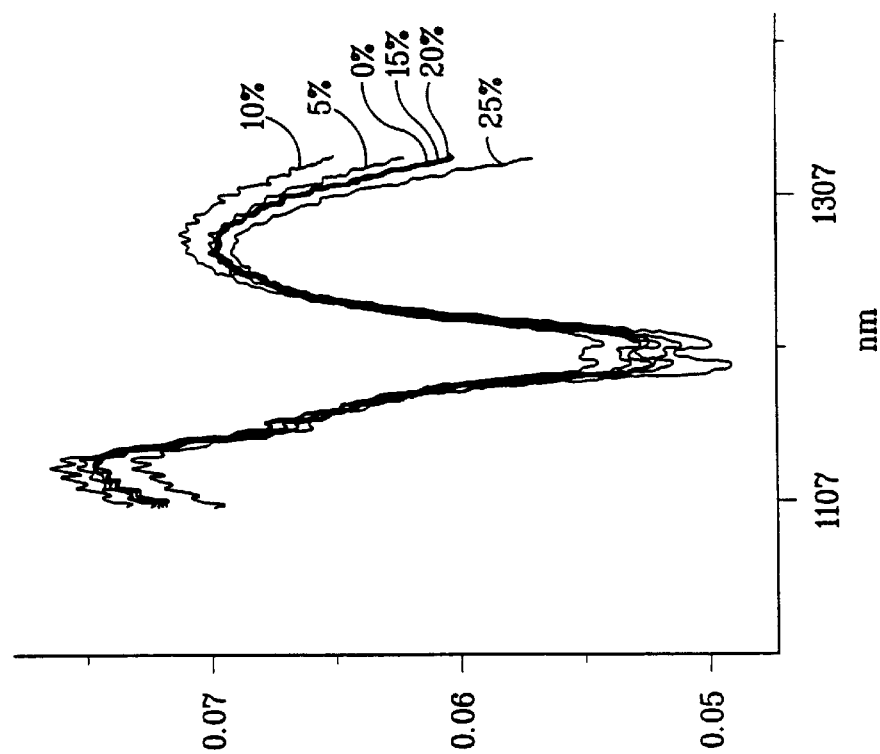
FIG. 14 is a plot of normalized light intensity versus wavelength based on the data shown in FIG. 13. The X-axis is the wavelength in nanometers. The Y-axis is the response in arbitrary units.
Figure 13:
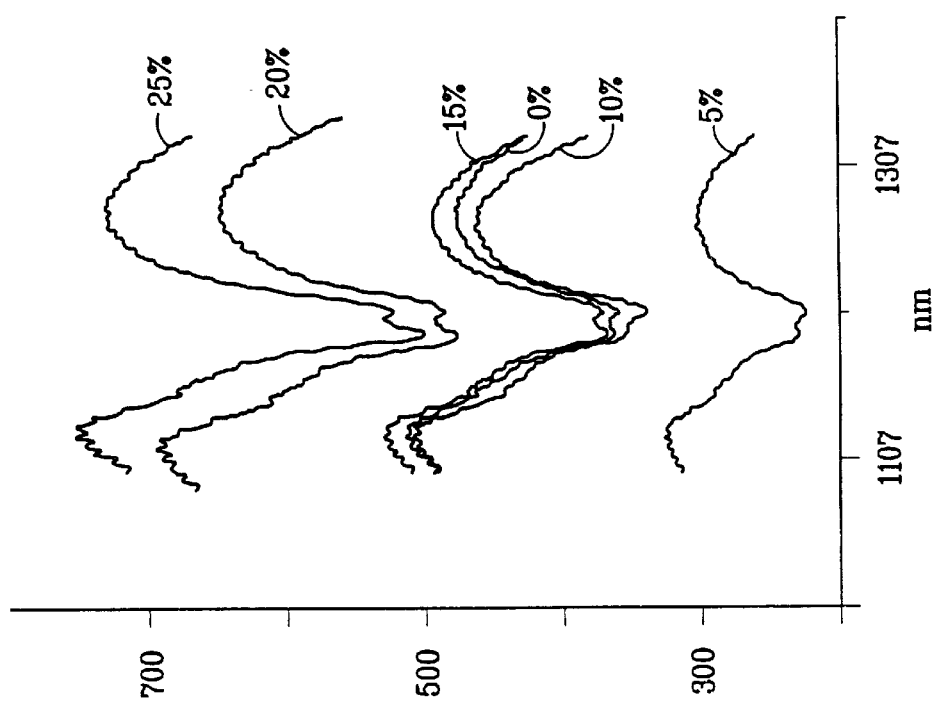
FIG. 13 is a plot of measured light intensity versus wavelength for isooctane/oil/water mixtures ranging from 0–25% isooctane using the near-IR attenuation method. The X-axis is the wavelength in nanometers. The Y-axis is the instrument's response in arbitrary units.

A mixture composed of 67% oil and 33% water was prepared as a starting point. Using the set up shown in FIG. 5, the mixture was analyzed using the near-IR attenuation method. Light from a quartz tungsten halogen lamp 16 having strong emissions in the near-IR range was the directed to the mixture and analyzed by the InGaAs diode array. Additional measurements were taken as isooctane was subsequently added until a concentration of 25% isooctane was achieved. The intensity was measured at each wavelength in the 1100 nm to 1300 nm range (a total of 200 wavelengths). FIG. 13 shows the raw spectra taken from the mixtures of crude oil, water, and isooctane. The measured intensities were normalized using the spectrum vector lengths. The resulting normalized spectra are shown in FIG. 14.

Based upon the normalized spectra shown in FIG. 14, the weighting factors $\beta$ for each wavelength in the 1100 nm to 1300 nm range were determined (a total of 200 weighting factors) using a partial least squares regression technique, discussed below. Based on these weighting factors, an algorithm was developed in the form of equation 5 (linear, with $\alpha=1$) for the calculation of the concentration of "gas" (i.e., isooctane), $C_{gas}$, in mixture n based on normalized intensity IN a each wavelength in the 1100 nm to 1300 nm range:

$$C_{gas,n} = \beta_{gas,1100\ nm} IN_{n,1100\ nm} + \beta_{gas,1101\ nm} IN_{n,1101\ nm} + \ldots + \beta_{gas,1520\ nm} IN_{n,1520\ nm} \quad [8]$$

A leave one out analysis revealed a standard error for this algorithm of only 0.55% in the percentage in the percentage concentration value.

C. Determination Of Weighting Factors

Once the spectral data are normalized to remove the effects of scattering, any one of a number of well know regression techniques, some of which are discussed below, can be used to determine the weighting factors $\beta$ to be used in weighing the values of the normalized component intensities measured in actual service in order to calculate concentration. The preferred regression technique is partial least squares regression. In some cases, two or more techniques may be employed—for example, an initial regression model may be determined based on a partial least squares regression technique and then refined using a multiple least squares regression technique.

Univariate regression is by far the most familiar technique for correlating spectral data to concentration. In chemical analysis this amounts to correlating the value of the peak spectral intensity $IN_n$ of spectrum n with the concentration $C_n$ of the constituent k of interest associated with that spectrum. The sequence of observations of $IN_n$ and $C_n$ from mixtures at each of the concentrations to be used in the calibration are used to derive a linear equation:

$$C_n = \beta \cdot IN_n + b \quad [9]$$

where:

$\beta$–the slope of the linear equation b=the concentration at zero intensity (i.e., the y-axis intercept)

This equation is optimized by minimizing the sum of the squares of the differences (residuals) between the predicted and true values; minimizing the residuals being one of the common threads that ties the various forms of regression together. These values of $\beta$ and b thus developed are used in equation 5 to determine the concentration of constituent k—for example, oil—in actual service. These calculations would be repeated for other constituents for which concentration was to be calculated—for example, gas—so that a equation in the form shown in equation 5 would be derived for each constituent, with each constituent having different values for the weighting factor $\beta$ and b.

Although univariate least squares regression is computationally simple, it will not offer sufficient accuracy in most applications since only the normalized intensities at one wavelength (that at which the intensity is a maximum) are used in the model. Therefore, more sophisticated regression techniques, such as those discussed below are preferred.

Multiple least squares (MLS) regression is another well known regression technique. Although the goal of MLS regression is identical to univariate least squares, i.e., to minimize the sum of the squares of the residuals, it allows more than one variable (i.e., normalized intensities at more than one wavelength) to be used in the regression analysis:

$$C = \beta_0 + \beta_1 \cdot IN_1 + \beta_2 \cdot IN_2 + \ldots + \beta_m \cdot IN_m + e \quad [10]$$

where m refers to the total number of collected wavelengths i and e represents the error of the simple model. The coefficients $\beta$ are essentially weighting factors that relate how much information each measured intensity, at each individual wavelength, contains concerning the concentration C. The largest values of the weighting factors $\beta$ are associated with the wavelengths that have the most influence on the determination of concentration.

MLS regression is an adequate procedure in some situations. However, it requires independence of the elements in the matrix subject to inversion—an unlikely situation for collinear spectroscopic data. Also, significant amounts of irrelevant information are likely to be incorporated into the model since every variable is included in the model.

In recent years, principal component regression (PCR) methods have been used to solve a wide variety of chemical problems which require the use of multivariate analysis. PCR involves decomposition of a row matrix containing the normalized intensity spectra into a loading matrix and a score matrix so that the product of these two matrices yields the original normalized intensity spectra. Each row vector in the loading matrix is referred to as a principal component and consists of a single loading value L for each spectral wavelength. Hence, the first row vector in the loading matrix corresponds to principal component 1 ($PC_1$), the second row to $PC_2$, and so on.

The magnitude of a particular loading for a given principle component indicates how much information that wavelength contributes to the principle component. Inspection of the loading matrix may reveal which wavelengths contain the most information about the concentration of the constituent of interest. The scores matrix simply relates the principal components back to the original spectra, i.e., the scores define how much a particular principal component contributes to a spectrum. Thus the first row vector of the scores matrix tells how much $PC_1$, $PC_2$, etc., contribute to the particular spectrum. The principal components are ranked in order of variance, i.e. $PC_1$ accounts for the greatest amount of variance in the set of input spectra. For this reason, the vast majority of the spectral information is included in the first few principal components, while the higher principal components are comprised mostly of noise.

The reduction of data dimension and the elimination of noise makes PCR the obvious choice over MLS regression. However, PCR suffers from a disadvantage in that the correlation between the property of interest and the spectral intensities is not included in the generation of the principle components.

Partial least squares (PLS) regression, also known as Projection to Latent Structures, is described, for example, in Wold, "Partial Least Squares," in Encyclopedia of Statistic Sciences, Vol. 6, Katz and Johnson, Ed. (Wiley 1985), pp. 581–591 and Manne, "Analysis of Two Partial-Least-Squares Algorithms for Multivariant Calibration," Chemom. Intell. Lab. Syst. (1987) 2:187–197, each of which is hereby incorporated by reference. PLS regression is a procedure that simultaneously estimates the eigenvectors in both the spectral data and the sample property data. Although PLS regression is fundamentally similar to PCR, it has the additional advantage of ordering its factors by considering both the variance of the spectral data and its correlation to the property of interest. Generally, this results in an equivalent or slightly more reliable model than PCR generates. An additional advantage of PLS regression involves a much faster computation time (when using a bidiagonalization procedure) compared to PCR. PLS regression shares many PCR characteristics—for example, PLS regression finds factors analogous to PCR's principal components. However, because these factors contain information about the correlations, they often yield more parsimonious and, in some situations, more reliable models than PCR.

Although PLS regression is preferred, other regression techniques could also be utilized, such as classical least squares, or inverse least squares in addition to any of the other techniques discussed above. For example, neural net regression techniques could also be used, especially if the regression model were nonlinear. A number of regression techniques suitable for use in practicing the current invention are described more fully in R. Kramer, "Chemometric Techniques For Quantitative Analysis," ISB 0-824-0198-4, Marcel Dekker (1998), incorporated by reference herein.

Regardless of the regression technique utilized, a separate regression is performed for each constituent so that a weighting factors $\beta_i$ is obtained for each of the selected wavelengths to be used in the algorithm for each constituent.

D. Determination of the Wavelengths to be Used in the Algorithm

As previously discussed, in performing the calibration and constructing the algorithm, component intensities are preferably measured at each wavelength within a preselected range of wavelengths—for example, in the experiments discussed above, algorithms were constructed using the normalized intensity for each wavelength within the 1100 to 1520 nm range for oil using the near-IR absorption method, within the 18 to 770 pixels range for oil using the fluorescence method, and within the 1100 to 1300 nm range for gas using the near-IR absorption method. The weighting factor associated with many of these wavelengths (i.e., those whose intensities can not be readily relied upon to determine concentration of the constituent of interest), however, will be very close to zero. Therefore, if desired in order to simply the computations, the algorithm can be constructed by selecting only key wavelengths within the range—specifically, those wavelengths whose intensities contain the maximum amount of information concerning the concentration of the constituents of interest.

According to the current invention, a variety of methods may be used to select the key wavelengths to be included in the algorithm, such as by inspection of the weighting factors in the algorithm. As previously discussed, the larger the variation in the intensity of the component of the emerging light at a given wavelength as the concentration of a particular constituent varies, relative to the intensity variation at that wavelength as the concentration of other constituents varies, the larger the weighting factor $\beta_{ki}$ for that particular constituent at that wavelength. A large weighting factor means that the value of the intensity of the light at that wavelength will carry significant information about the concentration of interest.

Preferably, the wavelengths to be used in the algorithm are determined using a "leave one out" validation technique. This is accomplished by performing the calibration calculations discussed above using all but one of the mixtures for which data is available but so as to develop an algorithm containing only one wavelength—the wavelength having the highest weighting factor $\beta$. This algorithm is then used to predict the concentration for the mixture excluded from the calibration and the resulting error determined. The calibration calculations are then re-run but this time including the mixture previously excluded but leaving out a different mixture so as to develop another single-wavelength algorithm. Again the error associated with the predicted concentration for the new excluded mixture is determined. This process is repeated until each of the mixtures in the calibration have been left out. The predicted residual error sum of the squares (PRESS) associated with this one wavelength algorithm is then calculated.

The calculations above are then repeated using an algorithm containing the wavelengths having the two highest weighting factors, and the PRESS associated with these algorithms is calculated. The calculations are then repeated adding one additional wavelength to the algorithm each time until an algorithm containing all of the wavelengths has been constructed. The algorithm that results in the lowest value for PRESS contains the optimum number of wavelengths.

E. Multiple Algorithms for Different Concentration Ranges

Figure 12:
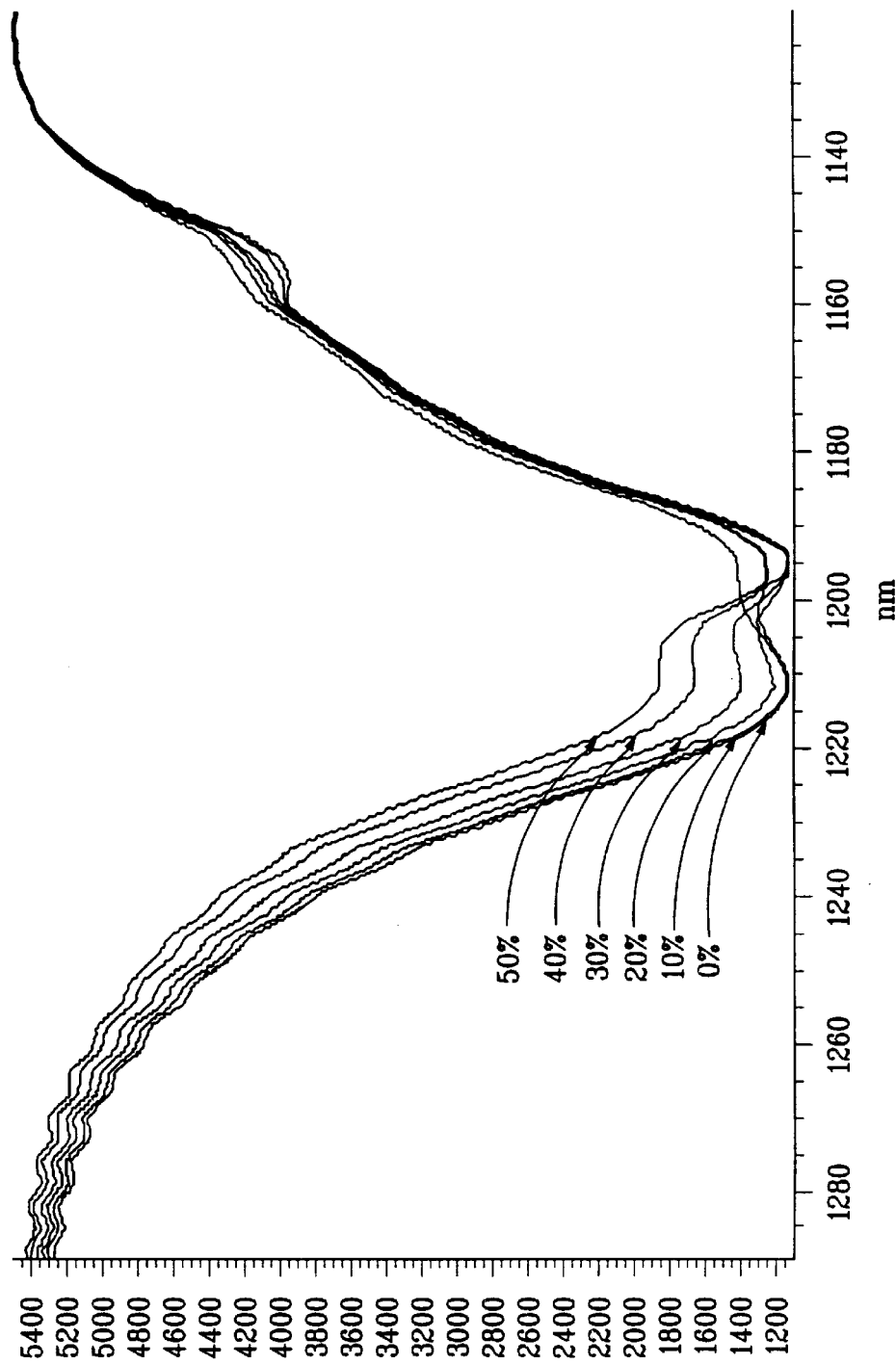
FIG. 12 is a plot of measured light intensity versus wavelength for isooctane/oil/water mixtures ranging from 0–50% isooctane using the near-IR attenuation method. The X-axis is the wavelength in nanometers. The Y-axis is the response in arbitrary units.

Calibration results can be improved if the algorithms are limited to certain concentration ranges. This can be accomplished by performing separate regression analyses for mixtures in concentrations within predetermined ranges—for example,. mixtures ranging between 0% to 50% oil are used in one regression to arrive at one algorithm and mixtures ranging between 50% to 100% oil are used in another regression to arrive at another algorithm—rather than using all of the mixtures from 0% to 100% in a single regression. For example, the near-IR calibration data shown in FIGS. 6 and 7 were re-analyzed using the same partial least squares regression technique but, this time, the analysis was performed separately for the 0% to 50% oil concentration range and the 50% to 100% oil concentration range so as to develop two different algorithms, one for each range. This reduced the 2.9% standard error that resulted from the use of a single algorithm, previously discussed, to a 1.6% for the 0% to 50% range and to 1.4% for the 50% to 100% range. Similarly, re-analyzing the near-IR fluorescence calibration data shown in FIGS. 11 and 12 separately for the 0% to 50% and 50% to 100% ranges reduced the standard error from 5.6% to 3. 1% for the 0% to 50% range and to 2.1% for the 50% to 100% range.

Particularly in the case of oil wells, those skilled in the art will realize that both the near-IR attenuation data and the near-IR fluorescence data may be significantly dependent on the pressure and temperature of the fluid stream being analyzed, which may be at pressures and temperatures as high as 400° F. and 20,000 psig. Thus, in some applications, it may be desirable to compensate for pressure and temperature effects by performing the calibration on mixtures at the pressures and temperatures expected to be encountered in actual service, or on mixtures of varying pressures and temperatures so as to arrive at a set of algorithms, each of which is applicable to a different ranges of pressures and/or temperatures. In this case, classification models can be constructed using mixtures compositions of varying pressure and temperature so that the light component data from the flowing fluid can be assigned to a concentration algorithm that has been optimized for the pressures and temperatures having ranges that encompass those of the flowing fluid.

V. Use of Downhole Fluid Analysis in an Oil Well

By way of example only, the invention will be described in connection with the analysis of the fluid flowing from a multilateral well into which production strings have been incorporated. It will be understood by those skilled in the art that the invention is equally applicable to other environments in which it is desirable to remotely sense the presence of a substance that fluoresces or absorbs radiation, such as oil, in a flowing fluid.

Figure 16:
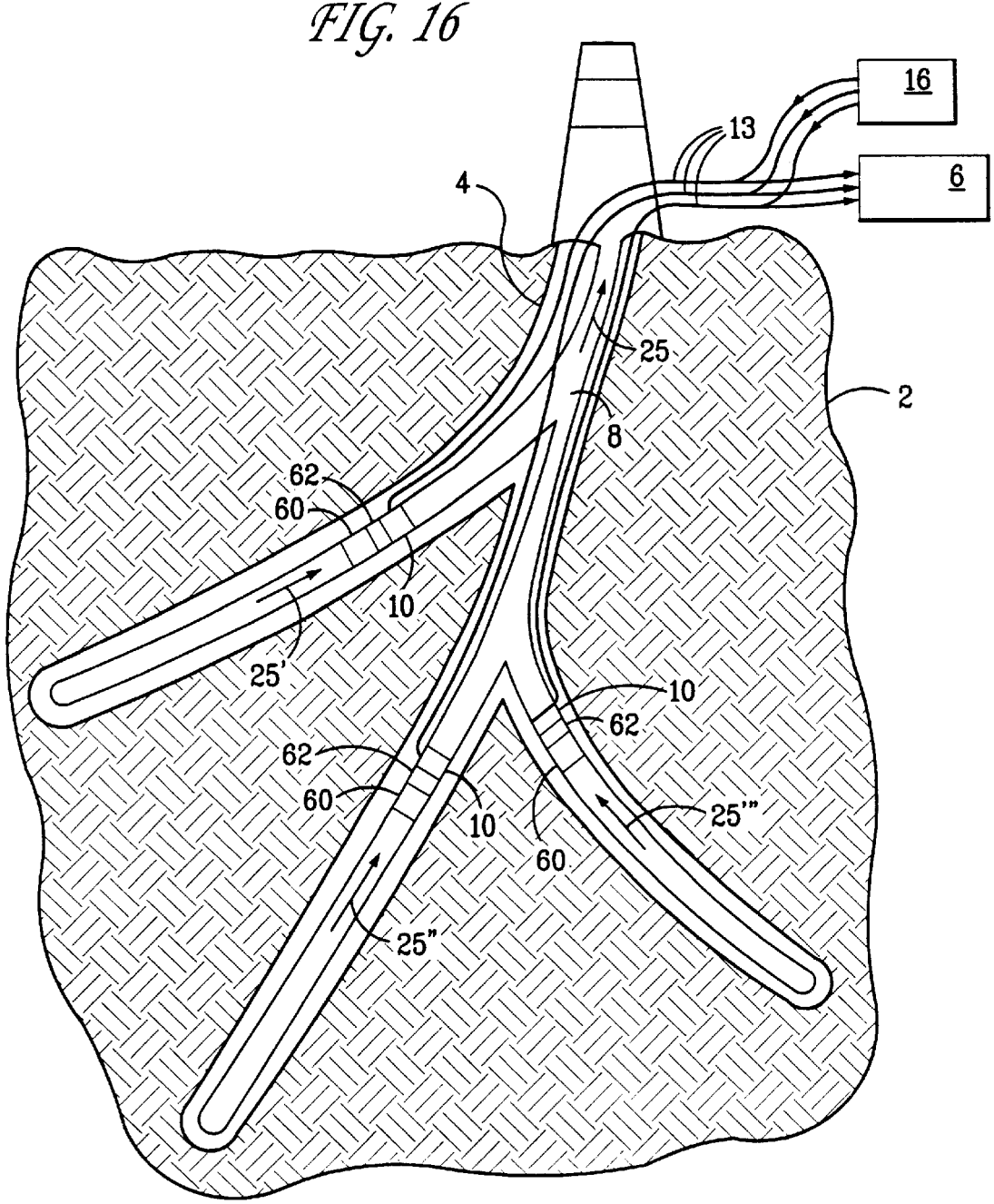
FIG. 16 is a schematic diagram of a multilateral well into which downhole fluid analyzers according to the current invention have been incorporated.

As depicted in FIG. 16, a multilateral well 4 has three zones extending into the formation 2. A section of a production string 8 is located in each zone so that all three zones produce fluids simultaneously. Each section of the production string 8 includes a valve 70 for regulating the flow of fluid from its zone. The fluid 25 flowing from the well 4 typically may comprise one or more of oil, water, natural gas, and solids, such as sand. As is conventional, the fluid 25', 25" and 25''' from all three zones are combined into a common flow line 25 before reaching the surface. As a result, an analysis of the fluid at the surface according to a conventional approach will not enable the operator to assess the production of the individual zones of the well.

A system for analyzing fluid according to the current invention is shown incorporated into each zone of the well 4. Specifically, an instrumented section 10 of the type shown in FIG. 1 have been incorporated into the branches of the production piping that extend into each zone of the well, along with a mixer 60 and diverter 62. As shown in FIG. 16, fiber optic cables 14, which may be several kilometers long, connect each of the instrumented sections 10 to the light source 16 and fluid analyzer 6 at the surface.

As previously discussed, the computer 20 of the fluid analyzer 6 is programed with an appropriate algorithm for calculating the concentrations of oil and water, each of which is preferably in the form of equation [5] so that it employs weighting factors for selected wavelengths, which are preferably determined based on a calibration of the oil from the well.

As shown in FIGS. 1 and 15, during production, the light source 16 periodically or continuously transmits light to each of the sensors 12 in the instrumented sections 10 via the optical fibers 14'. The intensity of the components of the collected light returned from each of the sensors 12 by the optical fibers 14" over a predetermined range of wavelengths is measured using the spectrographic detector 18. The computer 20 periodically or continuously calculates the concentrations of oil and water flowing through each of the zones of the well, using software that allows it to calculate the normalized intensity of the measured light components, preferably using one of the normalization techniques previously discussed, and then apply those normalized intensities to the aforementioned algorithms. The calculated concentrations of oil and water are then displayed by the indicator 24.

Incorporating instrumented sections 10 in each zone of the well 4 allows the operator to determine the percentage of oil and/or water in the fluid flowing downhole through each zone on a nearly real-time basis. This information can, in turn, be used to regulate the flow from each zone so as to optimize production, for example, by operating the valve 70 to reduce the flow from a zone producing a low percentage of crude oil, or excessive water.

Although the present invention has been discussed in connection with the determination of the concentration of crude oil or gas in an oil well producing an oil/water/gas mixture, the invention can be used to determine the concentration, or merely detect the presence, of oil or gas in other applications, such as when contamination of water by oil is suspected. Alternatively, the invention can be used to determine the concentration or detect the presence of other substances that fluoresce or absorb radiation in flowing streams that have scattering characteristics.

Moreover, although the mixer and diverter have been discussed in connection with the sensor of a fluid analyzer, these components could also be used in connection with other types of sensors used in the well piping.

Accordingly, the present invention may be embodied in other specific forms without departing from the spirit or essential attributes thereof and, accordingly, reference should be made to the appended claims, rather than to the foregoing specification, as indicating the scope of the invention.

What is claimed:

1. A method of determining the concentration of at least one predetermined constituent in a fluid flowing through a downhole portion a well, comprising the steps of:

a) generating a beam of light;

b) directing said beam of light into said fluid flowing through said downhole portion of said well so as to cause one portion of said light to be absorbed by said fluid and another portion of said light to travel through said fluid and emerge from said fluid, said emerging light having been scattered by said fluid and comprised of a plurality components each of which has a different wavelength;

c) transmitting at least a portion of said light that traveled through said fluid and emerged therefrom to a location proximate to the surface of the earth;

d) measuring the intensity of each of at least a portion of said components of said transmitted light, each of said light components in said portion of light components having a wavelength falling within a predetermined range of wavelengths, said light component intensity measurements being conducted at said location proximate said surface;

e) normalizing at least those of said measured light component intensities having selected wavelengths by dividing said intensities by a characteristic derived from said measured component intensities so as to reduce the effect of said scattering of said light components;

f) raising each of said normalized light component intensities at said selected wavelengths by a respective exponent, said exponents being any non-zero numbers;

g) multiplying each of said exponentially raised normalized light component intensities at said selected wavelengths by a predetermined weighting factor based upon its respective wavelength so as to obtain a weighted and normalized light component intensity at each of said selected wavelengths; and h) combining said weighted and normalized light component intensities at said selected wavelengths so as to calculate said concentration of said constituent.

2. The method according to claim 1, wherein said characteristic by which said measured components intensities are normalized is derived from all of said measured component intensities at all wavelengths at which said component intensities are measured.

3. The method according to claim 2, wherein the step of normalizing said component intensities comprises dividing each of said component intensities at said selected wavelengths by the vector length of said measured component intensities.

4. The method according to claim 3, wherein said vector length is calculated from the equation:

$$f = \sqrt{\sum_{i=1}^{m} I_i^2}$$

where:
- f=the vector length,
- i=represents the wavelength of each of said light components whose intensity is measured,
- $I_i$=the measured intensity of the light component having wavelength
- m=the total number of components whose intensities are measured.

5. The method according to claim 2, wherein the step of normalizing said component intensities comprises dividing each of said component intensities at said selected wavelengths by f, where:

$$f = \sum_{i=1}^{m} |I_i|$$

where:
- i=represents the wavelength of each of said light components whose intensity is measured,
- $I_i$=the measured intensity of the light component having wavelength i,
- m=the total number of components whose intensities are measured.

6. The method according to claim 2, wherein the step of normalizing said component intensities comprises dividing each of said component intensities at said selected wavelengths by the maximum measured intensity of said light components.

7. The method according to claim 1, wherein said constituent has at least one wavelength at which the absorption of light contacting said constituent peaks, and wherein said predetermined range of wavelengths within which the wavelengths of said measured components fall encompasses said absorption peak.

8. The method according to claim 1, wherein the step of transmitting at least a portion of said emerging light to said remote location comprises directing said portion of said emerging light through a fiber optic cable extending from said downhole location to said location proximate the surface of the earth.

9. The method according to claim 1, wherein the step of measuring said intensity of each of at least a portion of said components of said transmitted light is performed so that all of said intensities are measured simultaneously.

10. The method according to claim 1, wherein said selected wavelengths for which said component intensities are normalized in step (e) comprise a plurality of wavelengths selected based upon the extent to which the intensities of light components at said wavelengths are effected by variations in said concentration of said constituent.

11. The method according to claim 1, wherein said selected wavelengths for which said component intensities are normalized in step (e) comprise a plurality of wavelengths, and further comprising the step of selecting said plurality of wavelengths based upon the extent to which the intensities of light components at said wavelengths contribute to the prediction of said concentration of said constituent.

12. The method according to claim 11, wherein the step of selecting said plurality of wavelengths based upon the extent to which the intensities of light components at said wavelengths contribute to the prediction of said concentration of said constituent comprises the steps of:

i) directing a calibration beam of light into a plurality of fluid calibration mixtures so as to cause light to emerge from each of said calibration mixtures, each of said calibration mixtures containing predetermined varying concentrations of said constituent, said light emerging from said calibration mixtures comprised of components each of which has a different wavelength;

j) measuring the intensity of each of said components of said light emerging from said calibration mixtures having a wavelength falling within said predetermined range of wavelengths;

k) normalizing said measured intensities of said light components emerging from said calibration mixtures;

l) performing a regression analysis on said normalized intensities of said calibration mixtures.

13. The method according to claim 1, wherein at least a portion of said respective exponents by which said normalized light component intensities are raised in step (f) have a value that is not equal to 1.

14. The method according to claim 1, wherein each of said respective exponents by which said normalized light component intensities are raised in step (f) has a value equal to 1.

15. The method according to claim 1, wherein at least a portion of said of said weighting factors are negative.

16. The method according to claim 1, wherein said wavelengths at which said component intensities are measured in step (d) comprises each of said wavelengths within said predetermined range of wavelengths.

17. The method according to claim 16, wherein said predetermined range of wavelengths encompasses at least a portion of the near infrared range.

18. The method according to claim 17, wherein said selected wavelengths for which said component intensities are normalized in step (e) comprise every wavelength at which said component intensity is measured.

19. The method according to claim 17, wherein said selected wavelengths for which said component intensities are normalized in step (e) comprise less than every wavelength at which said component intensity is measured.

20. The method according to claim 18, wherein said selected wavelengths for which said component intensities are normalized in step (e) comprise at least two wavelengths.

21. The method according to claim 1, wherein said selected wavelengths for which said component intensities are normalized in step (e) comprise each wavelength at which said component intensity is measured.

22. The method according to claim 1, wherein said selected wavelengths for which said component intensities are normalized in step (e) comprise less than every wavelength at which said component intensity is measured.

23. The method according to claim 1, wherein said selected wavelengths for which said component intensities are normalized in step (e) comprise at least two wavelengths.

24. The method according to claim 1, further comprising the step of determining said weighting factors by:

i) directing a calibration beam of light into a plurality of fluid calibration mixtures so as to cause light to emerge from each of said calibration mixtures, each of said calibration mixtures containing predetermined varying concentrations of said constituent, said light emerging from said calibration mixtures comprised of components each of which has a different wavelength;

j) measuring the intensity of each of said components of said light emerging from said calibration mixtures having a wavelength falling within said predetermined range of wavelengths;

k) normalizing at least a selected portion of said measured intensities of said light components emerging from said calibration mixtures;

l) performing a regression analysis on said normalized intensities of said calibration mixtures so as to determine said weighting factors.

25. The method according to claim 1, wherein said constituent is oil.

26. The method according to claim 1, wherein said constituent is natural gas.

27. The method according to claim 1, wherein said constituent is water.

28. The method according to claim 1, wherein said beam of light directed into said fluid is comprised of at least one component having a wavelength in the near infrared range.

29. The method according to claim 1, wherein said beam of light directed into said fluid is comprised of components having wavelengths that encompass at least a portion of the near infrared range.

30. The method according to claim 1, wherein said predetermined range of wavelengths within which the wavelengths of said measured components fall comprises at least a portion of the near-infrared range.

31. The method according to claim 1, wherein the step of combining said weighted and normalized light component intensities at said selected wavelengths so as to calculate said concentration of said constituent comprises summing each of said weighted and normalized light component intensities at said selected wavelengths.

32. A method of determining at a first location the concentration C of at least one predetermined constituent k in a fluid n located at a second location remote from the first location, comprising the steps of:

a) generating a beam of light proximate said first location;

b) transmitting said beam of light to said second location;

c) directing said beam of light into said fluid n at said second location so as to cause light to emerge from said fluid, said emerging light comprised of a plurality of components each of which has a different wavelength;

d) transmitting at least a portion of said emerging light to said first location;

e) measuring the intensity I of each of at least a portion of said components of said transmitted light at said first location, each of said light components having a wavelength falling within a predetermined range of wavelengths;

d) normalizing at least m measured light component intensities having selected wavelengths i so as to determine normalized light component intensities $IN_{in}$;

e) calculating said concentration C of said constituent k by inputting said normalized light component intensities into an equation of the form:

$$C_{kn} = \sum_{i=1}^{m} \beta_{ki} IN_{in}^{\alpha_{ki}} + b_k$$

where:
$\beta_{ki}$=Weighting factors for constituent k at wavelengths i
$\alpha_{ki}$=Exponents for constituent k at wavelengths i, at least a portion of said exponents being not equal to one, whereby said equation is non-linear
$b_k$=A constant for constituent k.

33. The method according to claim 32, wherein at least a portion of said weighting factors $\beta_i$ are equal to zero.

34. The method according to claim 32, wherein at least a portion of said exponents $\alpha_i$ are equal to 1.

35. The method according to claim 32, wherein the step of normalizing said component intensities at said selected wavelengths i comprises dividing each of selected component intensities by the vector length f of said measured component intensities, said vector length being calculated from the equation:

$$f = \sqrt{\sum_{i=1}^{m} I_i^2}$$

where:
$I_i$=the intensity of the light component having wavelength i.

36. The method according to claim 32, wherein said constituent has at least one wavelength at which the absorption of light contacting said constituent peaks, and wherein said predetermined range of wavelengths within which the wavelengths of said measured components fall encompasses said absorption peak.

37. The method according to claim 32, wherein at least one of the components of said light directed to said fluid has a wavelength that causes said constituent to emit fluorescent radiation so that at least a portion of said light emerging from said fluid comprises fluorescent radiation emitted by said fluid.

38. The method according to claim 32, wherein said second location is downhole in a well and said first location is proximate the surface of the earth.

39. An apparatus for determining the concentration of a predetermined constituent in a fluid flowing through a downhole portion a well, comprising:

a) means for generating a beam of light;

b) a section of pipe for directing the flow of said fluid flowing in said well toward the surface of the earth;

c) a sensor incorporated in the wall of said section of pipe, said sensor having (i) means for directing said beam of light into said fluid flowing through said downhole portion of said well so as to cause light to emerge from said fluid, said emerging light comprised of a plurality of components each of which having a different wavelength, said light emerging from said fluid having been scattered by said fluid prior to emerging therefrom, and (ii) means for collecting at least a portion of said light emerging from said fluid;

d) a fiber optic cable for transmitting at least a portion of said light collected by said sensor to a location proximate the surface of the earth;

e) means for measuring the intensity of each of said components of said transmitted light having a wavelength falling within a predetermined range of wavelengths at said location proximate the surface of the earth;

f) normalizing means for reducing the effect of said scattering of said light by dividing at least a selected portion of said measured component intensities by a characteristic derived from said measured component intensities;

g) means for multiplying each of said normalized light component intensities by a predetermined weighting factor based upon the respective wavelength of said light component so as to obtain weighted and normalized light component intensities; and h) means for determining said concentration of said constituent by combining said weighted and normalized selected light component intensities.

40. The apparatus according to claim 39, further comprising a mixer disposed in said well for mixing said fluid before said beam of light is directed into said fluid by said light beam directing means.

41. The apparatus according to claim 39, further comprising a diverter disposed in said well for diverting at least a portion of said fluid toward said means for measuring said component intensities.

42. The apparatus according 39, further comprising a computer, and wherein said means for means for normalizing said selected portion of said measured component intensities and said means for determining said concentration of said constituent comprises software program into said computer.

43. The apparatus according to claim 39, wherein said means for multiplying said normalized selected light component intensities by said predetermined weighting factors and said means for determining said concentration of said constituent by combining said weighted and normalized selected light component intensities comprises software programed into a computer.

44. The apparatus according to claim 39, further comprising means for raising each of said normalized light component intensities by a respective exponent, at least a portion of said exponents not being equal to one.

45. A method of determining the concentration of at least one predetermined constituent in a fluid flowing through a downhole portion a well, comprising the steps of:

a) generating a beam of light;

b) directing said beam of light into said fluid flowing through said downhole portion of said well so as to cause light to emerge from said fluid, said light directed into said fluid having at least one component having a wavelength that causes said constituent to emit fluorescent radiation so that at least a portion of said light emerging from said fluid comprises fluorescent radiation emitted by said fluid, said emerging light having been scattered by said fluid and comprised of a plurality of components each of which has a different wavelength;

c) transmitting at least a portion of said emerging light to a location proximate to the surface of the earth;

d) measuring the intensity of each of at least a portion of said components of said transmitted light, each of said light components in said portion of light components having a wavelength falling within a predetermined range of wavelengths, said light component intensity measurements being conducted at said location proximate said surface;

e) normalizing at least those of said measured light component intensities having selected wavelengths by dividing said intensities by a characteristic derived from said measured component intensities, so as to reduce the effect of said scattering of said light components;

f) raising each of said normalized light component intensities at said selected wavelengths by a respective exponent, said exponents being any non-zero numbers;

g) multiplying each of said exponentially raised normalized light component intensities at said selected wavelengths by a predetermined weighting factor based upon its respective wavelength so as to obtain a weighted and normalized light component intensity at each of said selected wavelengths; and h) combining said weighted and normalized light component intensities at said selected wavelengths so as to calculate said concentration of said constituent.

46. The method according to claim 45, wherein said beam of light directed into said fluid is essentially monochromatic, and wherein the step of normalizing said measured component intensities comprises dividing each of said measured component intensities by the intensity of said measured light component having a wavelength equal to that of said essentially monochromatic beam of light.

47. The method according to claim 45, wherein said beam of light directed to said fluid is essentially monochromatic.

48. The method according to claim 47, wherein said monochromatic beam of light directed to said fluid has a wavelength of approximately 852 nm.

49. The method according to claim 45, wherein at least a portion of said respective exponents by which said normalized light component intensities are raised in step (f) have a value that is not equal to one.

50. The method according to claim 45, wherein each of said respective exponents by which said normalized light component intensities are raised in step (f) has a value equal to one.

51. The method according to claim 45, wherein said selected wavelengths for which said component intensities are normalized in step (e) comprise less than every wavelength at which said component intensity is measured.

52. A method of determining the concentration of at least one predetermined constituent in a fluid flowing through a downhole portion of a well, comprising the steps of:

a) generating a beam of light;

b) directing said beam of light into said fluid flowing through said downhole portion of said well so as to cause light to emerge from said fluid, said emerging light having been scattered by said fluid and comprised of a plurality of components each of which has a different wavelength;

c) transmitting at least a portion of said emerging light to a location proximate to the surface of the earth;

d) measuring the intensity of each of at least a portion of said components of said transmitted light, each of said light components in said portion of light components having a wavelength falling within a predetermined range of wavelengths, said light component intensity measurements being conducted at said location proximate said surface;

e) normalizing only those of said measured light component intensities that have wavelengths corresponding to a selected predetermined set of wavelengths, so as to produce normalized light component intensities at only said predetermined wavelengths, said predetermined set of wavelengths selected by:

(A) directing a calibration beam of light into a plurality of fluid calibration mixtures so as to cause light to emerge from each of said calibration mixtures, each of said calibration mixtures containing predetermined varying concentrations of said constituent, said light emerging from said calibration mixtures comprised of components each of which has a different wavelength;

(B) measuring the intensity of at least a portion of said components of said light emerging from said calibration mixtures;

(C) normalizing said measured intensities of said light components emerging from said calibration mixtures;

(D) performing a regression analysis on said normalized intensities of said calibration mixtures;

f) multiplying by predetermined weighting factors only said normalized light component intensities at said predetermined set of wavelengths, so as to obtain a set of weighted and normalized light component intensity at each of said wavelengths in said predetermined set of wavelengths; and h) combining said weighted and normalized light component intensities at said predetermined set of wavelengths so as to calculate said concentration of said constituent.

53. The apparatus according to claim 52, further comprising means for raising each of said normalized light component intensities by a respective exponent, at least a portion of said exponents not being equal to one.

* * * * *

UNITED STATES PATENT AND TRADEMARK OFFICE
CERTIFICATE OF CORRECTION

PATENT NO. : 6,507,401 B1
DATED : January 14, 2003
INVENTOR(S) : Turner et al.

It is certified that error appears in the above-identified patent and that said Letters Patent is hereby corrected as shown below:

<u>Column 14,</u>
Line 12, please delete "$IN_{in}=IN_{in}/fn$" and insert therefor -- $IN_{in}=I_{in}/fn$ --;

<u>Column 22,</u>
Line 5, please delete "$C=\beta_o+\beta_1 \cdot IN_1+\beta_2 \cdot IN_2+\ldots+\beta_{m \cdot INm}+e$" and insert therefor
-- $C=\beta_o+\beta_1 \cdot IN_1+\beta_2 \cdot IN_2+\ldots+\beta_m \cdot IN_m+e$ --;

Signed and Sealed this

Eighteenth Day of November, 2003

JAMES E. ROGAN
*Director of the United States Patent and Trademark Office*

UNITED STATES PATENT AND TRADEMARK OFFICE
CERTIFICATE OF CORRECTION

| | | |
|---|---|---|
| PATENT NO. | : 6,507,401 B1 | Page 1 of 1 |
| APPLICATION NO. | : 09/453003 | |
| DATED | : January 14, 2003 | |
| INVENTOR(S) | : William Edward Turner et al. | |

It is certified that error appears in the above-identified patent and that said Letters Patent is hereby corrected as shown below:

Column 1, line 6, Insert the following prior to the first paragraph:

This invention was made with Government support under DE-AC26-98FT40481 awarded by the U.S. Department of Energy. The Government has certain rights in the invention.

Column 14,
Line 12, please delete "$IN_{in}=IN_{in}/fn$" and insert therefor --$IN_{in}=I_{in}/fn$--;

Column 22,
Line 5, please delete "$C=\beta_o+\beta_1 \cdot IN_1+\beta_2 \cdot IN_2+...+\beta_{m \cdot INm}+e$" and insert therefor
--$C=\beta_o+\beta_1 \cdot IN_1+\beta_2 \cdot IN_2+...+\beta_m \cdot IN_m+e$--;

Signed and Sealed this

Twenty Second Day of April, 2008

JON W. DUDAS
*Director of the United States Patent and Trademark Office*